United States Patent [19]
Tso et al.

[11] Patent Number: 5,834,597
[45] Date of Patent: *Nov. 10, 1998

[54] MUTATED NONACTIVATING IGG2 DOMAINS AND ANTI CD3 ANTIBODIES INCORPORATING THE SAME

[75] Inventors: J. Yun Tso, Menlo Park; Michael S. Cole, San Francisco, both of Calif.; Claudio Anasetti, Mercer Island, Wash.

[73] Assignee: Protein Design Labs, Inc., Mountain View, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 656,586

[22] Filed: May 31, 1996

Related U.S. Application Data

[63] Continuation-in-part of Ser. No. 650,410, May 20, 1996, abandoned.

[51] Int. Cl.[6] .................................................. C07K 16/00
[52] U.S. Cl. ............................................................ 530/387.3
[58] Field of Search ........................................... 530/378.3

[56] References Cited

U.S. PATENT DOCUMENTS 5,585,089  12/1996  Owen et al. ........................ 424/133.1

OTHER PUBLICATIONS

Anasetti Claudio et al., "Induction of Specific Nonresponsiveness in Unprimed Human T Cells by Anti–CD3 Antibody and Alloantigen," *J. Exp. Med.,* Dec. 1990, vol. 172, pp. 1693–1700.

Anasetti Claudio et al., "Treatment of Acute Graft–Versus–Host Disease With a Nonmitogenic Anti–CD3 Monoclonal Antibody," *Translation,* Nov. 1992, vol. 54, No. 5, pp. 844–851.

Jolliffe Linda K., "Humanized Antibodies: Enhancing Therapeutic Utility Through Antibody Engineering," *Intern. Rev. Immunol.,* 1993, vol. 10, pp. 241–250.

Alegre, M.L. et al. 1994. Transplantation, 57:1537–1543.
Lurd, J. et al. 1991. J. Immunol. 147:2657–2662.
Pakkeu, PWHI. et al. 1992. J. Immunol. 148:695–701.

*Primary Examiner*—Lila Feisee
*Assistant Examiner*—Minh-Tan David
*Attorney, Agent, or Firm*—Townsend and Townsend and Crew

[57] ABSTRACT

The invention provides mutated IgG2 constant regions and anti-CD3 antibodies incorporating the same. Such antibodies specifically bind to the CD3 antigen on T-cells but induce reduced mitogenic response compared with otherwise identical antibodies bearing natural IgG2 constant regions. The antibodies can be used for treating disorders requiring immune suppression with fewer side effects than result from treatment with prior anti-CD3 antibodies.

18 Claims, 14 Drawing Sheets

```
ATG GAT TTT CAA GTG CAG ATT TTC AGC TTC CTG CTA ATC AGT GCC TCA GCC ATA ATA TCC
 M   D   F   Q   V   Q   I   F   S   F   L   L   I   S   A   S   A   I   I   S                60

AGA GGA CAA ATT GTT CTC ACC CAG TCT CCA GCA ATC ATG TCT GCA TCT CCA GGG GAG AAG
 R   G   Q   I   V   L   T   Q   S   P   A   I   M   S   A   S   P   G   E   K          120
         =

GTC ACC ATG ACC TGC AGT GCC AGC TCA AGT GTA AGT TAC ATG AAC TGG TAC AAG CAG AAG
 V   T   M   T   C   S   A   S   S   S   V   S   Y   M   N   W   Y   K   Q   K          180

TCA GGC ACC TCC CCC AAA AGA TGG ACT TAT GAC ACA TCC AAA CTG GCT TCT GGA GTC CCT
 S   G   T   S   P   K   R   W   T   Y   D   T   S   K   L   A   S   G   V   P          240

GCT CGC TTC AGT GGC AGT GGG TCT GGG ACC TCT TAC TCT CTC ACA ATC AGC AGC ATG GAG
 A   R   F   S   G   S   G   S   G   T   S   Y   S   L   T   I   S   S   M   E          300

GCT GAA GAT GCT GCC ACT TAT TAC TGC CAG CAG TGG AGT AGT AAC CCA CCC ACG TCC GGC
 A   E   D   A   A   T   Y   Y   C   Q   Q   W   S   S   N   P   P   T   S   G          390

TCG GGG ACA AAG TTG GAA ATA AAA
 S   G   T   K   L   E   I   K
```

FIG. 1A

```
ATG GAA AGG CAC TGG ATC TTT CTA CTC CTG TCA GTA ACT GCA GGT GTC CAC TCC CAG   60
 M   E   R   H   W   I   F   L   L   L   S   V   T   A   G   V   H   S   Q

GTC CAG CTG CAG CAG TCT GGG GCT GAA CTG GCA AGA CCT GGG GCC TCA CTG AAG ATG TCC  120
 V   Q   L   Q   Q   S   G   A   E   L   A   R   P   G   A   S   L   K   M   S

TGC AAG GCT TCT GGC TAC ACC TTT ATT AGT TAC ACG ATG CAC TGG GTA AAA CAG AGG CCT  180
 C   K   A   S   G   Y   T   F   I   S   Y   T   M   H   W   V   K   Q   R   P

GGA CAG GGT CTG GAA TGG ATT GGA TAC ATT AAT CCT AGA AGT GGT TAT ACT CAT TAC AAT  240
 G   Q   G   L   E   W   I   G   Y   I   N   P   R   S   G   Y   T   H   Y   N

CAG AAG TTA AAG GAC AAG GCC ACA TTG ACT GCA GAC AAA TCC TCC AGC ACA GCC TAC ATG  300
 Q   K   L   K   D   K   A   T   L   T   A   D   K   S   S   S   T   A   Y   M

CAA CTG AGC AGC CTG ACA TCT GAG GAC TCT GCA GTC TAT TAC TGT GCA AGA TCG GCC TAC  360
 Q   L   S   S   L   T   S   E   D   S   A   V   Y   Y   C   A   R   S   A   Y

TAT GAT TAT GAC GGC TTT GCT TAC TGG GGC CAA GGG ACT CTG GTC ACT GTC TCT GCA
 Y   D   Y   D   G   F   A   Y   W   G   Q   G   T   L   V   T   V   S   A

FIG. 1B
```

```
ATG GAG ACC GAT ACC CTC CTG CTA TGG GTC CTC CTG CTA TGG GTC CCA GGA TCA ACC GGA    60
 M   E   T   D   T   L   L   L   W   V   L   L   L   W   V   P   G   S   T   G

GAT ATT CAG ATG ACC CAG TCT CCA TCC CTC TCT GCT AGC GTC GGG GAT AGG GTC ACC        120
 D   I   Q   M   T   Q   S   P   S   L   S   A   S   V   G   D   R   V   T
 =

ATA ACC TGC TCT GCC AGT TCA AGT GTA AGT TAC ATG AAC TGG TAC CAG CAG AAG CCA GGC    180
 I   T   C   S   A   S   S   V   S   Y   M   N   W   Y   Q   Q   K   P   G
         ─────────────────────────────────────────────────

AAA GCT CCC AAG AGA CTA ATT TAT GAC ACA TCC AAA CTG GCT TCT GGA GTC CCT TCT AGG    240
 K   A   P   K   R   L   I   Y   D   T   S   K   L   A   S   G   V   P   S   R
                             ───────────────

TTC AGT GGC AGT GGA TCT GGG ACC GAT TTC ACC CTC ACA ATC AGC TCT CTG CAG CCA GAA    300
 F   S   G   S   G   S   G   T   D   F   T   L   T   I   S   S   L   Q   P   E

GAT TTC GCC ACT TAT TAC TGC CAG CAA TGG AGT AGT AAC CCA CCC ACG TTC GGT GGA GGG    360
 D   F   A   T   Y   Y   C   Q   Q   W   S   S   N   P   P   T   F   G   G   G
                         ─────────────────────────────

ACC AAG GTG GAG ATC AAA
 T   K   V   E   I   K
```

FIG. 1C

```
ATG GGA TGG AGC TGG ATC TTT CTC TTC CTC CTG TCA GGT ACC GCG GGC GTG CAC TCT CAG     60
 M   G   W   S   W   I   F   L   F   L   L   S   G   T   A   G   V   H   S   Q

GTC CAG CTT GTC CAG TCT GGG GCT GAA GTC AAG AAA CCT GGC GCC AGC GTG AAG GTC TCC    120
 V   Q   L   V   Q   S   G   A   E   V   K   K   P   G   A   S   V   K   V   S

TGC AAG GCT TCT GGC TAC ACC TTT ATT AGT TAC ACG ATG CAT TGG GTA AGG CAG GCC CCT    180
 C   K   A   S   G   Y   T   F   I   S   Y   T   M   H   W   V   R   Q   A   P

GGA CAG GGT CTG GAA TGG ATG GGA TAT ATT AAT CCG AGA AGT GGG TAT ACT CAT TAC AAT    240
 G   Q   G   L   E   W   M   G   Y   I   N   P   R   S   G   Y   T   H   Y   N

CAG AAG TTA AAG GAC AAG GCA ACA CTT ACC GCG GAC AAA TCC GCG AGC ACA GCC TAC ATG    300
 Q   K   L   K   D   K   A   T   L   T   A   D   K   S   A   S   T   A   Y   M

GAA CTG AGC AGC CTG AGA TCT GAG GAC ACC GCA GTC TAT TAC TGT GCA AGA TCG GCC TAC    360
 E   L   S   S   L   R   S   E   D   T   A   V   Y   Y   C   A   R   S   A   Y

TAT GAT TAT GAC GGC TTT GCT TAC TGG GGC CAA GGA ACC CTG GTC ACA GTC TCC TCA
 Y   D   Y   D   G   F   A   Y   W   G   Q   G   T   L   V   T   V   S   S
```

FIG. 1D

| HUMAN ISOTYPE | RESIDUE NUMBER | | | |
|---|---|---|---|---|
| | 234 | 235 | 236 | 237 |
| IgG1 | Leu | Leu | Gly | Gly |
| IgG3 | Leu | Leu | Gly | Gly |
| IgG4 | Phe | Leu | Gly | Gly |
| IgG2 | Val | Ala | - | Gly |
| IgG2 mutant 1 | Ala | Ala | - | Gly |
| IgG2 mutant 2 | Val | Ala | - | Ala |
| IgG2 mutant 3 | Ala | Ala | - | Ala |
| IgG2 mutant 4 | Val | Glu | - | Ala |
| IgG2 mutant 5 | Ala | Glu | - | Ala |
| IgG4 AA mutant | Ala | Ala | Gly | Gly |

MUTATED NONACTIVATING IGG2 DOMAINS AND ANTI CD3 ANTIBODIES INCORPORATING THE SAME

THIS APPLN IS A CIP OF 08/650,410 May 20, 1996 NOW ABANDONED.

TECHNICAL FIELD

The invention applies the technical fields of immunology and molecular genetics to the design of mutated nonactivating IgG2 domains and humanized anti-CD3 antibodies incorporating the same.

BACKGROUND OF THE INVENTION

The CD3 complex on T cells is closely associated with the T cell receptor (TCR) heterodimer and plays an important role in T cell activation upon antigen binding. Certain anti-CD3 antibodies can activate T cells in the absence of antigen. Such activation depends on the interaction of the Fc portion of the monoclonal antibody (mAb) and the Fc receptors on accessory cells to crosslink CD3 complexes on T cells. Soluble anti-CD3 mAbs do not stimulate T cells to proliferate in vitro unless they are bound to plastic or to Fc receptor-bearing cells.

Although immunosuppression can be achieved by administering these antibodies to human subjects or mice, efficacy is often compromised by two factors. The first is the antiglobulin response resulting from multiple injections of foreign proteins, and the second is the first-dose syndrome resulting from T-cell activation. The symptoms include fever, chills, diarrhea and vomiting, and in severe cases have resulted in death. The syndrome is caused by release of a host of cytokines as a result of transient T-cell activation (see Abramowicz et al., *Transplantation* 47, 606, (1989)). Cytokines such as TNF-α, IFN-γ, IL-2, IL-4, IL-6 and GM-CSF have been implicated in these severe side-effects. In mice, two forms of anti-CD3 have been reported to be immunosuppressive without activating mouse T-cells: the F(ab')$_2$ form (see Hirsch et al., *Transplantation* 49, 1117, (1990)) and the chimeric form of the mouse IgG3 isotype (see Alegre et al., *J. Immunol.* 155, 1544, (1995)). The former lacks the portion of the constant region that binds Fcγ receptors, and the constant region of the latter has a low affinity for mouse Fcγ receptors.

In human therapy, it is desirable to have an anti-CD3 molecule that is not only humanized but also unable to interact with Fcγ receptors to minimize immunogenicity and toxicity. The respective affinities of various human IgG isotypes for the three Fcγ receptors, FcRI, FcRII, and FcRIII, have been determined (see Ravetch & Kinet, *Annu. Rev. Immunol.* 9, 457, (1991)). FcRI is a high affinity receptor that binds to IgGs in monomeric form, and the latter two are low affinity receptors that bind IgGs only in multimeric form. In general, both IgG1 and IgG3 have significant binding activity to all three receptors, IgG4 to FcRI, and IgG2 to only one type of FcRII called IIa$^{LR}$ (see Parren et al., *J. Immunol.* 148, 695 (1992); *J. Clin. Invest.* 90, 1537 (1992)). IIa$^{LR}$ is an allele of FcRII that is expressed in 40% of the Caucasian population. Several investigators have made chimeric anti-CD3 of various isotypes but all were reported to be mitogenic PBMCs (peripheral blood mononuclear cells) from at least some donors (see Bolt et al., *Eur. J. Immunol.*, 23, 403 (1993); Parren et al., *Res. Immunol.* 142, 793 (1991)). Hence, naturally occurring forms of Fc are unsuitable for producing nonactivating anti-CD3 mAbs.

Mutations made in the lower hinge/upper CH2 region in anti-CD3 IgG1 and IgG4 have been reported to render these molecules less mitogenic (see Alegre et al., *Transplantation* 57, 1537 (1994); Alegre et al., *J. Immunol.* 148, 3461 (1992)). A mutation at position 235 of IgG3 has been reported to affect its interaction with FcRI, and mutations at position 234 and 237 have been reported to affect its interaction with FcRII (see Lund et al., *J. Immunol.* 147, 2657, (1991)). An aglycosylated form of anti-CD3 has also been reported to have impaired binding to Fcγ receptors (see Bolt et al., *Eur. J. Immunol.* 23, 403 (1993)).

Notwithstanding these developments, there remains a need for anti-CD3 antibodies having mutated constant regions that exhibit mitogenic activity to a still lesser extent and/or in fewer patients than existing antibodies.

SUMMARY OF THE INVENTION

The invention provides mutated IgG2 constant regions comprising a nonnaturally occurring segment of amino acids between residues 234 and 237 defined by the EU numbering system. Anti-CD3 antibodies incorporating such IgG2 constant regions can specifically bind to CD3 antigens on T-cells without inducing a mitogenic response in the T-cells through specific binding to Fcγ receptors. In preferred mutated IgG2 constant regions residues 234, 235, and 237 form one of the following segments of amino acids: ala ala gly, val ala ala, ala ala ala, val glu ala, and ala glu ala. Note that position 236 (defined by the EU numbering system) is unoccupied in these mutated constant regions, as it is in a wildtype IgG2 constant region. Usually, the mutated segment is included in an otherwise naturally occurring human IgG2 constant region. The invention further provides anti-CD3 antibodies, preferably, humanized antibodies, incorporating the mutated IgG2 constant regions.

The invention further provides novel humanized antibodies derived from the mouse M291 antibody into which mutated IgG2 domains can be incorporated. A preferred humanized light chain comprises three complementarity determining regions (CDR1, CDR2 and CDR3) having amino acid sequences from the corresponding complementarity determining regions of the M291 immunoglobulin light chain, and a variable region framework from a human kappa light chain variable region framework sequence. A preferred humanized heavy chain comprises three complementarity determining regions (CDR1, CDR2 and CDR3) having amino acid sequences from the corresponding complementarity determining regions of M291 immunoglobulin heavy chain, and a variable region framework from a human heavy chain variable region framework sequence except in at least one position selected from a group consisting of H30, H67, H68, H70, H72 and H74 wherein the amino acid position is occupied by the same amino acid present in the equivalent position of the mouse M291 immunoglobulin heavy chain variable region framework. The immunoglobulin specifically binds to a CD3 antigen on the surface of T cells and usually has a binding affinity having a lower limit of about $10^7$ M$^{-1}$ and an upper limit of about five-times the binding affinity of the M291 immunoglobulin. Preferably, the humanized light chain variable region framework is from the light chain variable region framework of the HF2-1/17 antibody in subgroup I. Preferably, the humanized heavy chain region framework is from the heavy chain region variable framework of the 21/28 antibody. In this case, position H44 can be substituted with the same amino acid present in the equivalent position of a human immunoglobulin subgroup I consensus sequence.

BRIEF DESCRIPTION OF THE FIGURES

FIG. 1. Sequences of the cDNA (SEQ ID Nos:1,3,5 and 7) and translated amino acid sequences (SEQ ID NOs: 2,4,6 and 8) of the light chain (A,C) and heavy chain (B,D) variable regions of the mouse (A-B) or humanized (C-D) M291 antibody. The first amino acid of each mature chain is indicated by a double underline. The three CDRs in each chain are underlined.

Figure 2:
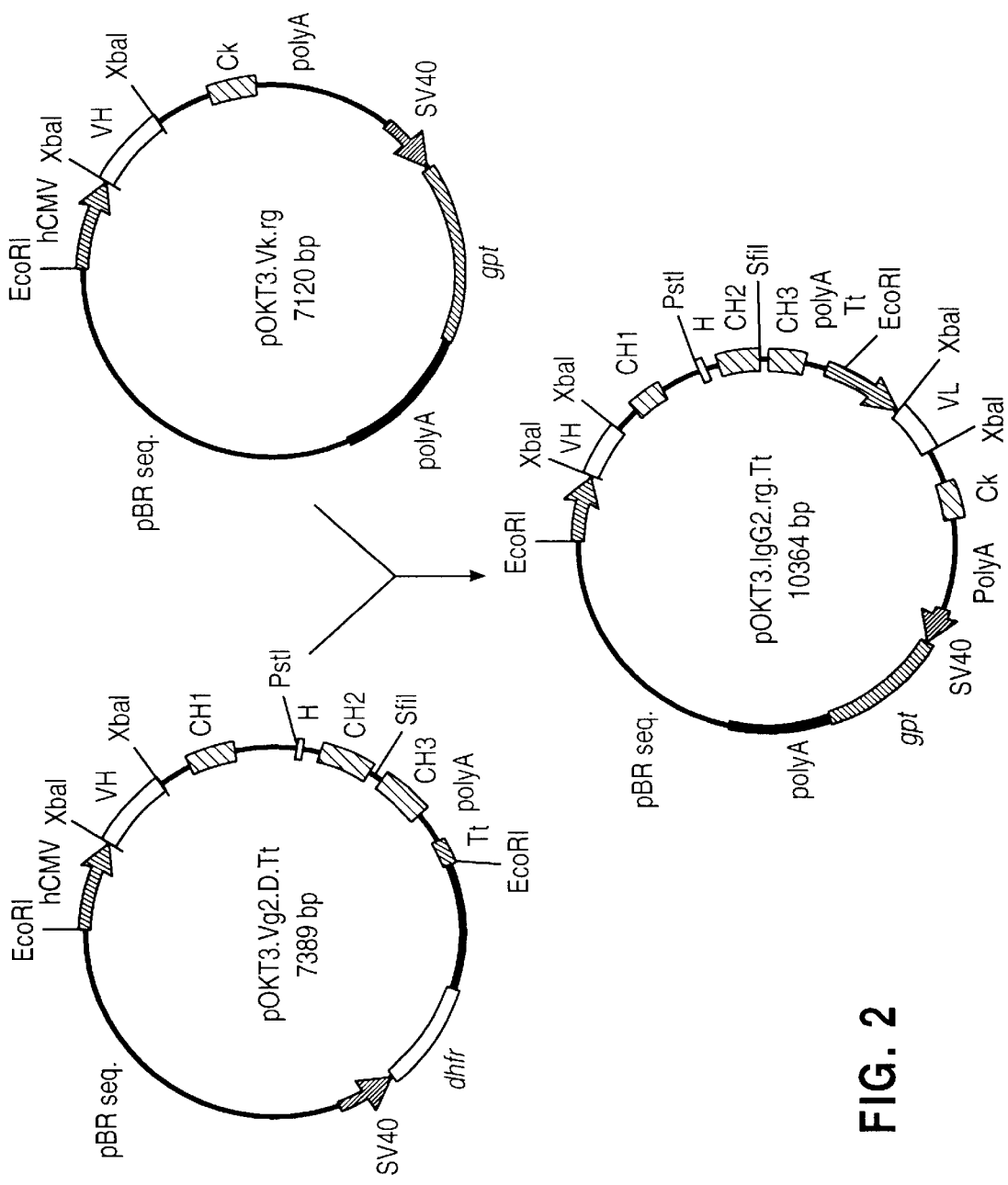

FIG. 2. Plasmid constructs expressing chimeric anti-CD3 antibodies. The $V_H$ and $V_L$ cDNAs of OKT3 were made into exons flanked by XbaI sites. The $V_L$ sequence was incorporated in an expression vector pvk.rg, and the $V_H$ sequence into the heavy chain expression vector, pVg2.D.Tt. The two plasmids were then recombined to generate one single plasmid coexpressing the heavy and light chains. PstI and SfiI sites are not unique in these plasmids.

FIG. 3. Sequences in the $C_H2$ region of the four human IgG isotypes, the five IgG2 mutants, and one IgG4 mutant. The EU numbering system was used for the residues.

FIG. 4. Amino acid sequence (SEQ ID NO:9) in the heavy chain constant region of IgG2 mutant 3. The $C_H1$ domain consists of residues 118–215, the hinge 216–230, the $C_H2$ 231–340, and the $C_H3$ 341–447. The symbol "–" indicates space introduced for the correct alignment with EU. Residues mutated from the wild type IgG2 are underlined. Except for residues 234–237, all five IgG2 mutants have identical sequences. The sequences in that region for the five mutants are shown in FIG. 3. All residues are named according to the EU numbering system.

Figure 5:
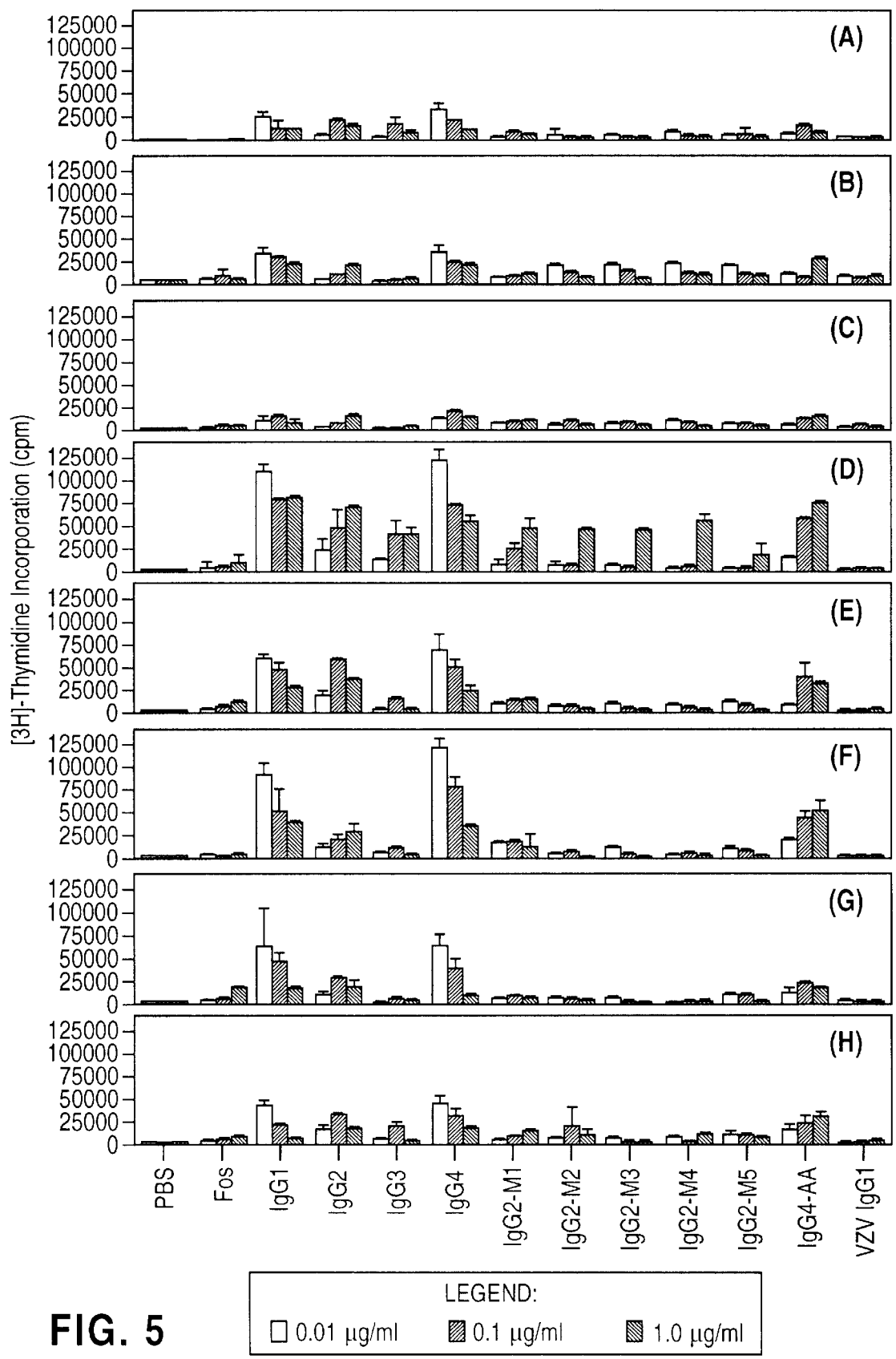

FIG. 5. T cell proliferation in response to chimeric OKT3 anti-CD3 antibodies. [$^3$H]-Thymidine incorporation by PBMCs from eight human donors (donors A–H) induced by chimeric anti-CD3 antibodies was determined. PBMCs were incubated with each anti-CD3 antibody at 10 ng/ml, 100 ng/ml, and 1 µg/ml for 72 hr, pulsed with [$^3$H]-thymidine for an additional 12 hr, and incorporation of the isotope was determined by scintillation counting. PBS is the phosphate buffered-saline control, Fos represents a F(ab')$_2$ version of the chimeric anti-CD3 molecule containing the leucine zipper Fos, M1–M5 refers to IgG2 mutants 1–5, AA to the Ala-Ala mutant of IgG4, and VZV IgG1 is a control irrelevant humanized antibody.

Figure 6:
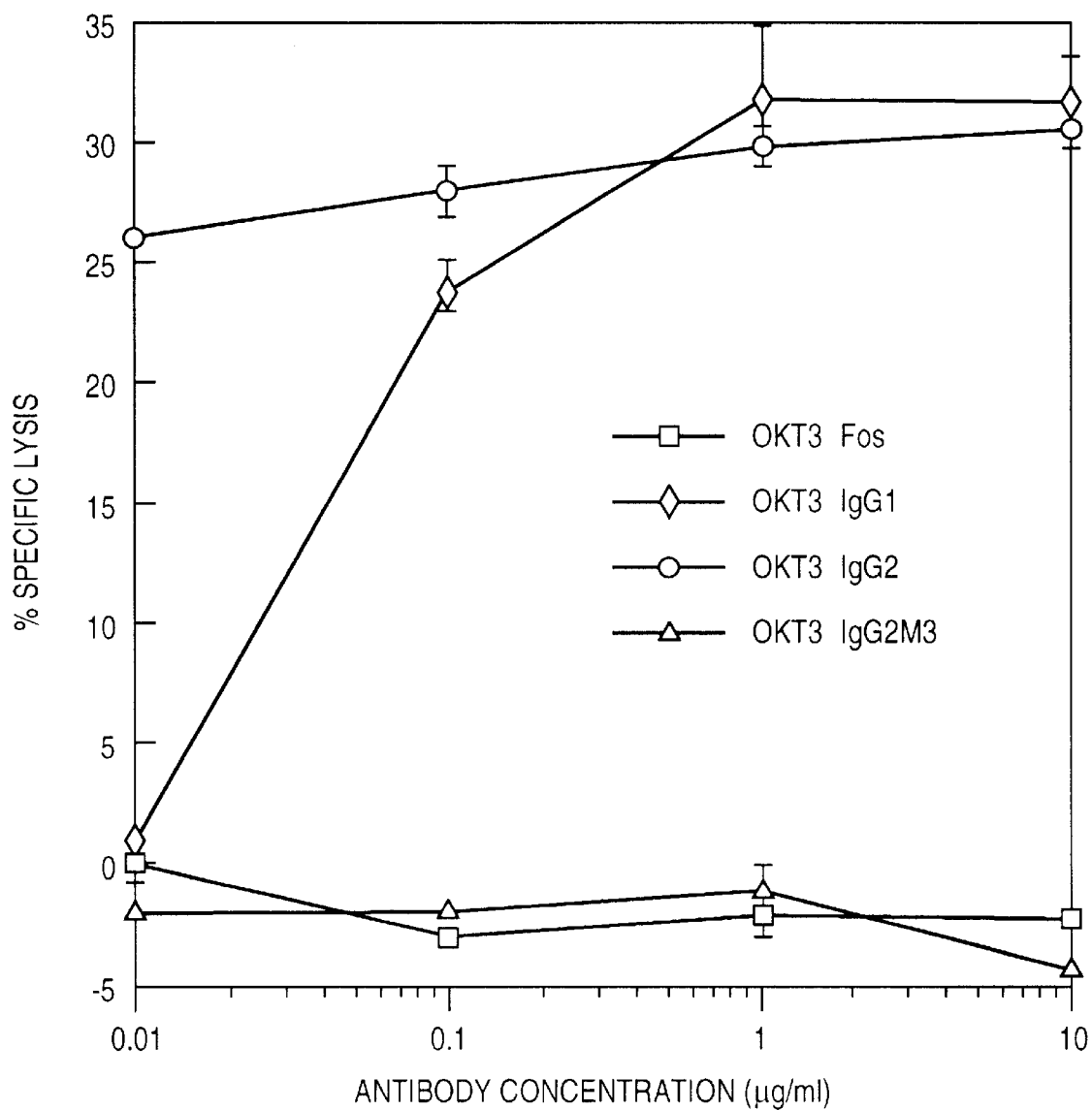

FIG. 6. Lysis by retargeted T cell blasts. [$^{51}$Cr]-labeled K562 cells and human T cell blasts were incubated with chimeric anti-CD3 antibodies at various concentrations for 4 hr and the release of $^{51}$Cr was measured. Fos represents a F(ab')$_2$ version of the chimeric anti-CD3 molecule.

Figure 7:
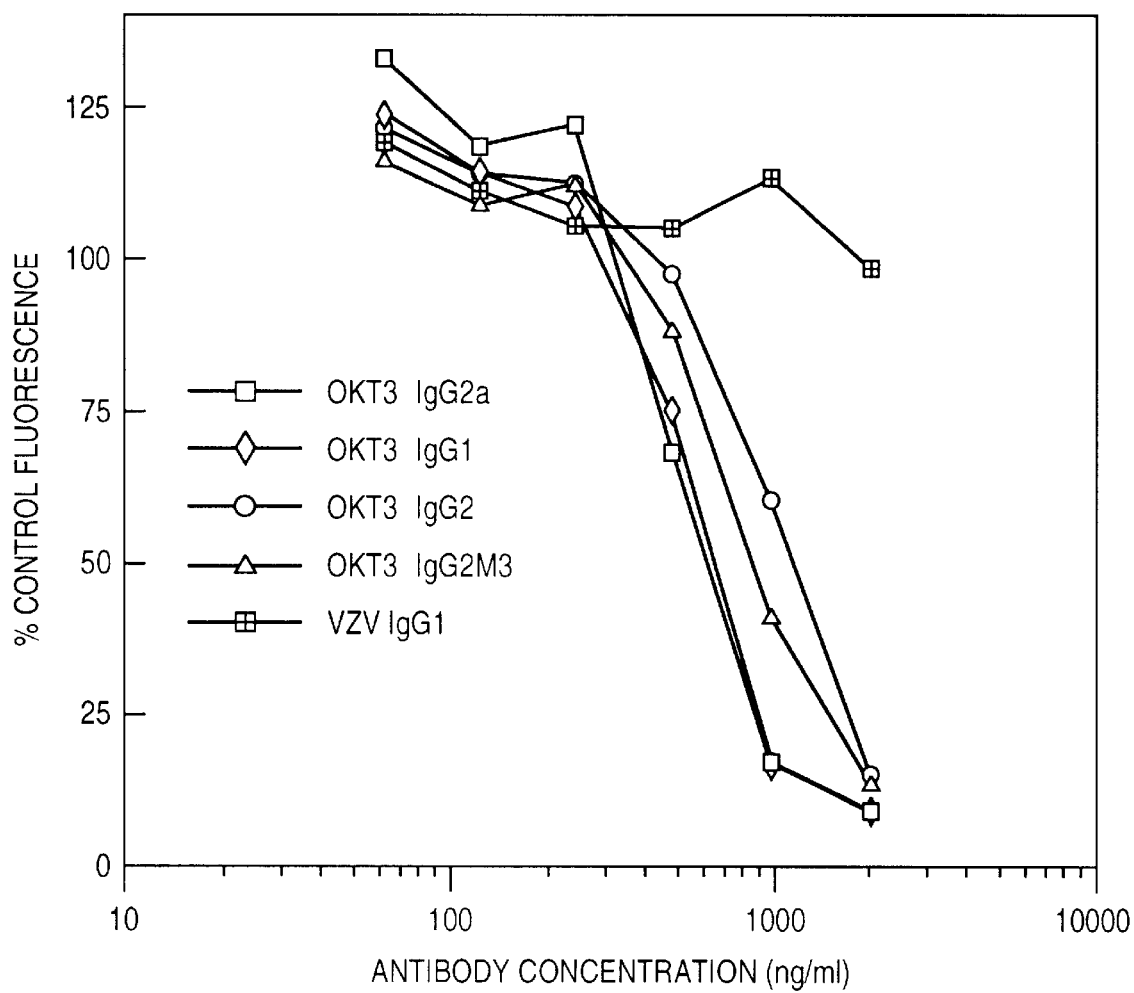

FIG. 7. Competition assay to compare the relative avidity of chimeric OKT3 anti-CD3 antibodies. Subsaturating amounts of murine OKT3-FITC on activated human T cells were displaced by increasing amounts of murine OKT3, or chimeric OKT3-IgG1, IgG2, and IgG2 mutant 3. VZV IgG1 is an irrelevant humanized antibody. Values are expressed in percent inhibition of fluorescence intensity when compared to that of the control without any competitive antibody.

Figure 8:
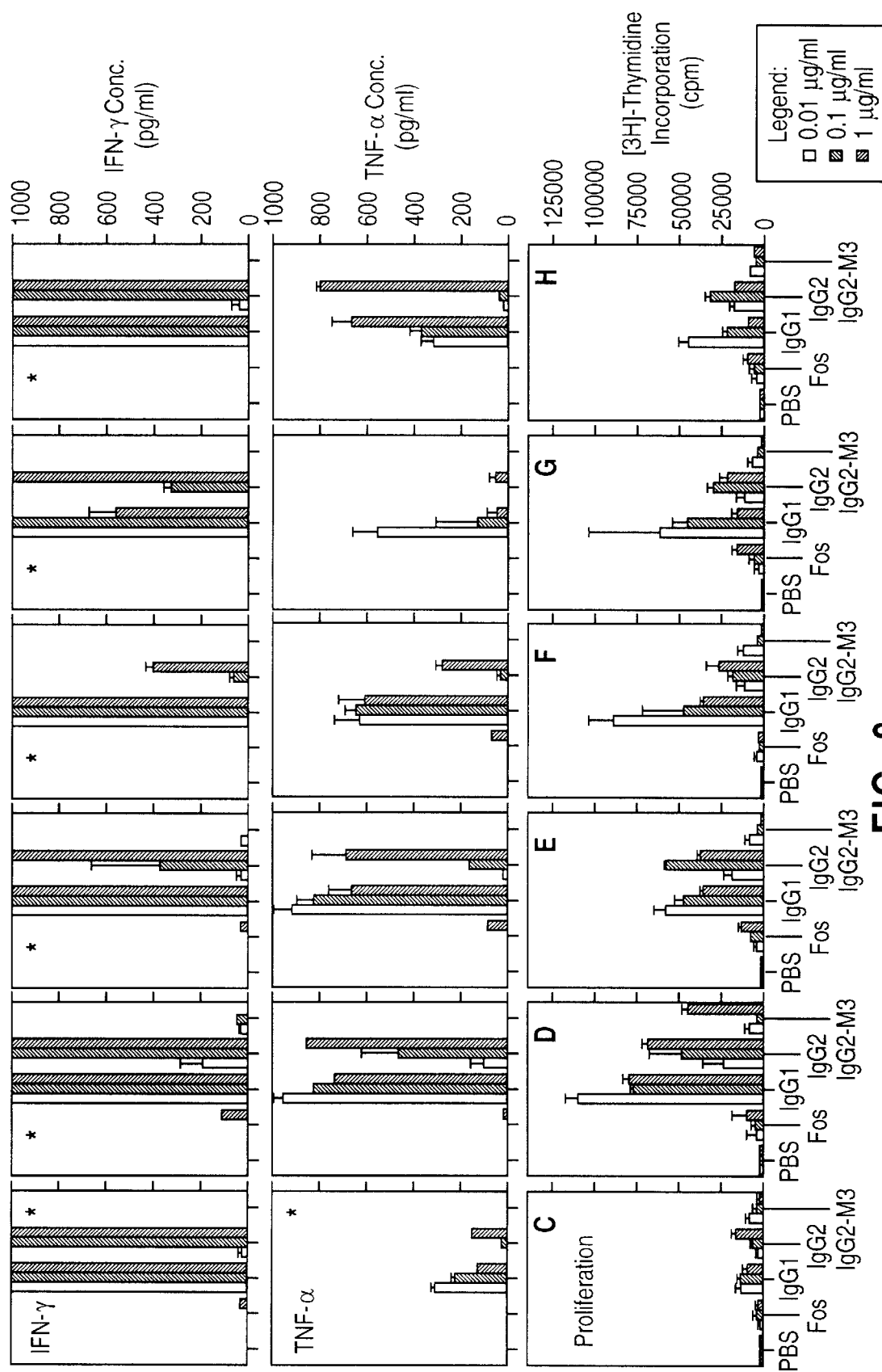

FIG. 8. Release of IFN-65 and TNF-α induced by chimeric OKT3 anti-CD3 antibodies. PBMCs from six human donors (donors C-H) were plated as in the T cell proliferation assay with three concentrations of each antibody. The concentration of IFN-γ was determined at 72 hr (upper panels), and TNF-60 at 24 hr (middle panels). The symbol (*) indicates that the concentration of the cytokine is beyond the upper limit of the assay. The T cell proliferation profiles of each donor to the antibodies tested are taken from FIG. 5 and are shown in the lower panels. The four antibodies used were chimeric OKT3 F(ab')$_2$ (Fos), IgG1, IgG2 and IgG2 mutant 3 (M3). PBS is the negative control without any antibody.

Figure 9:
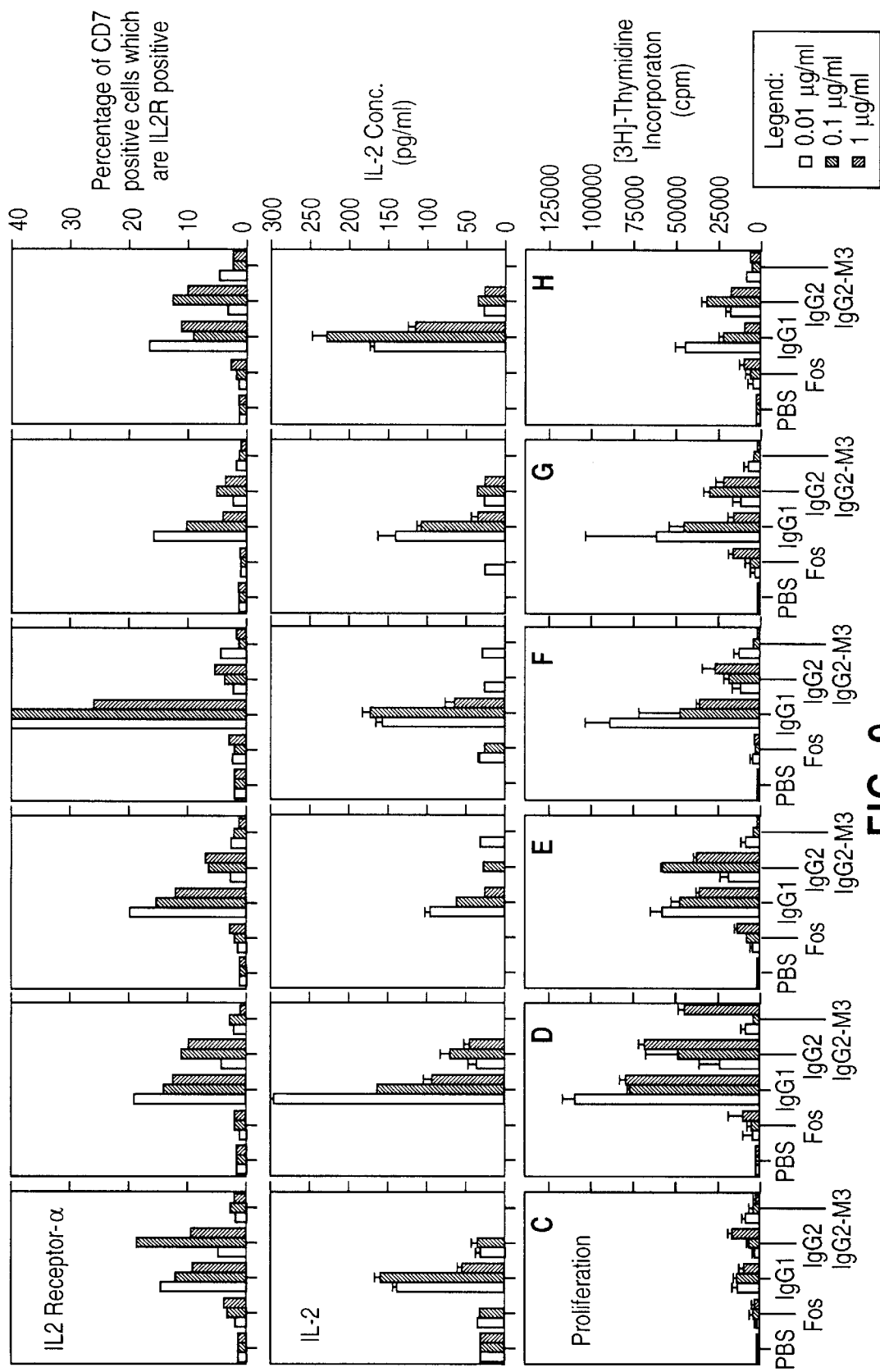

FIG. 9. Release of IL-2 and induction of the expression of IL-2 receptor-α (CD25) in T cells by chimeric OKT3 anti-CD3 antibodies. PBMCs from six human donors (donors C-H) were plated as in the T cell proliferation assay with three concentrations of each antibodies. The percentage of T cells (CD7-positive) expressing CD25 was determined by flow cytometry at 90 hr (upper panels), and the concentration of IL-2 was measured at 24 hr (middle panels). The T cell proliferation profiles of each donor to the antibodies tested are taken from FIG. 5 and are shown in the lower panels. The four antibodies used were anti-CD3 F(ab')$_2$ (Fos), IgG1, IgG2 and IgG2 mutant 3 (M3). PBS is the negative control without any antibody.

Figure 10:
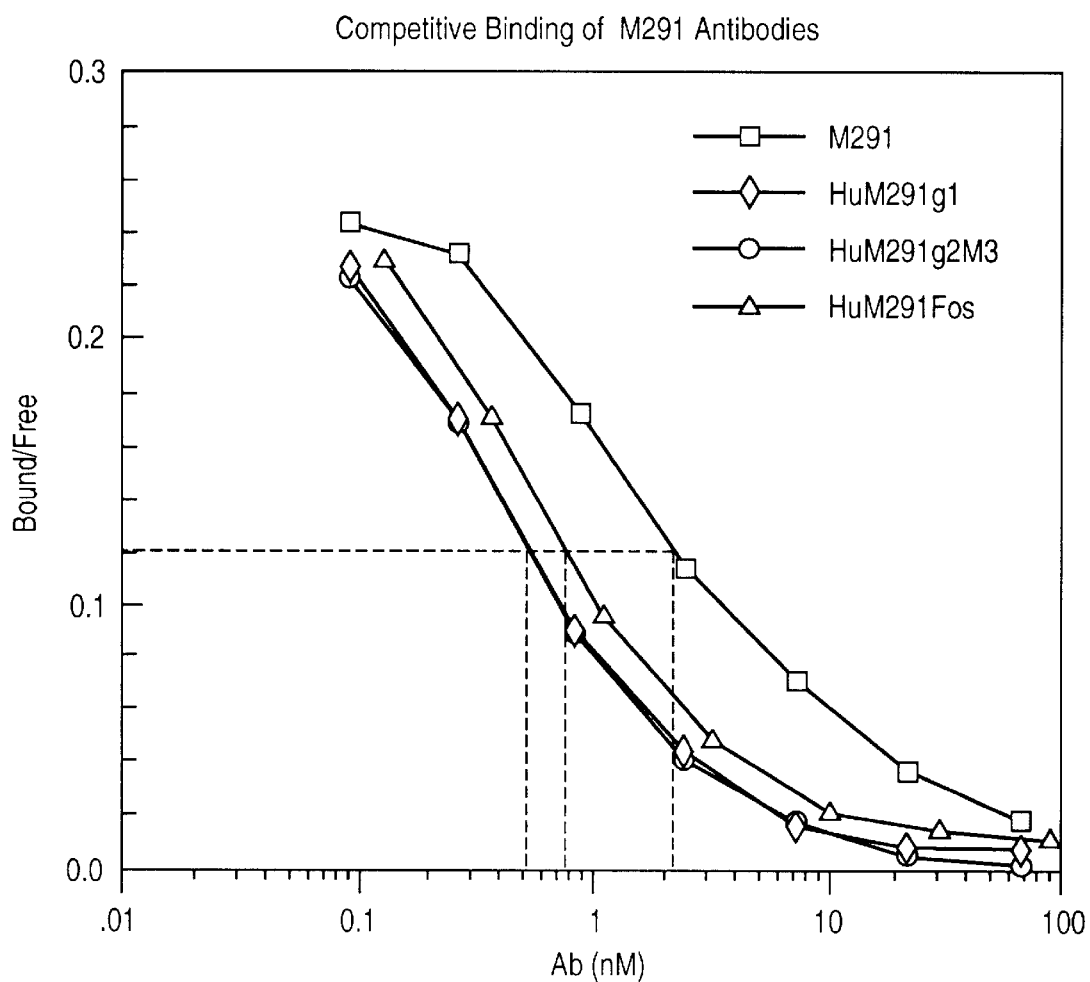

FIG. 10. Competitive binding of mouse and humanized M291 antibodies. Increasing concentrations of cold competitor antibodies were incubated with the T cells in the presence of radiolabeled tracer mouse M291 antibody, and the ratio of bound/free radioactivity determined.

Figure 11:
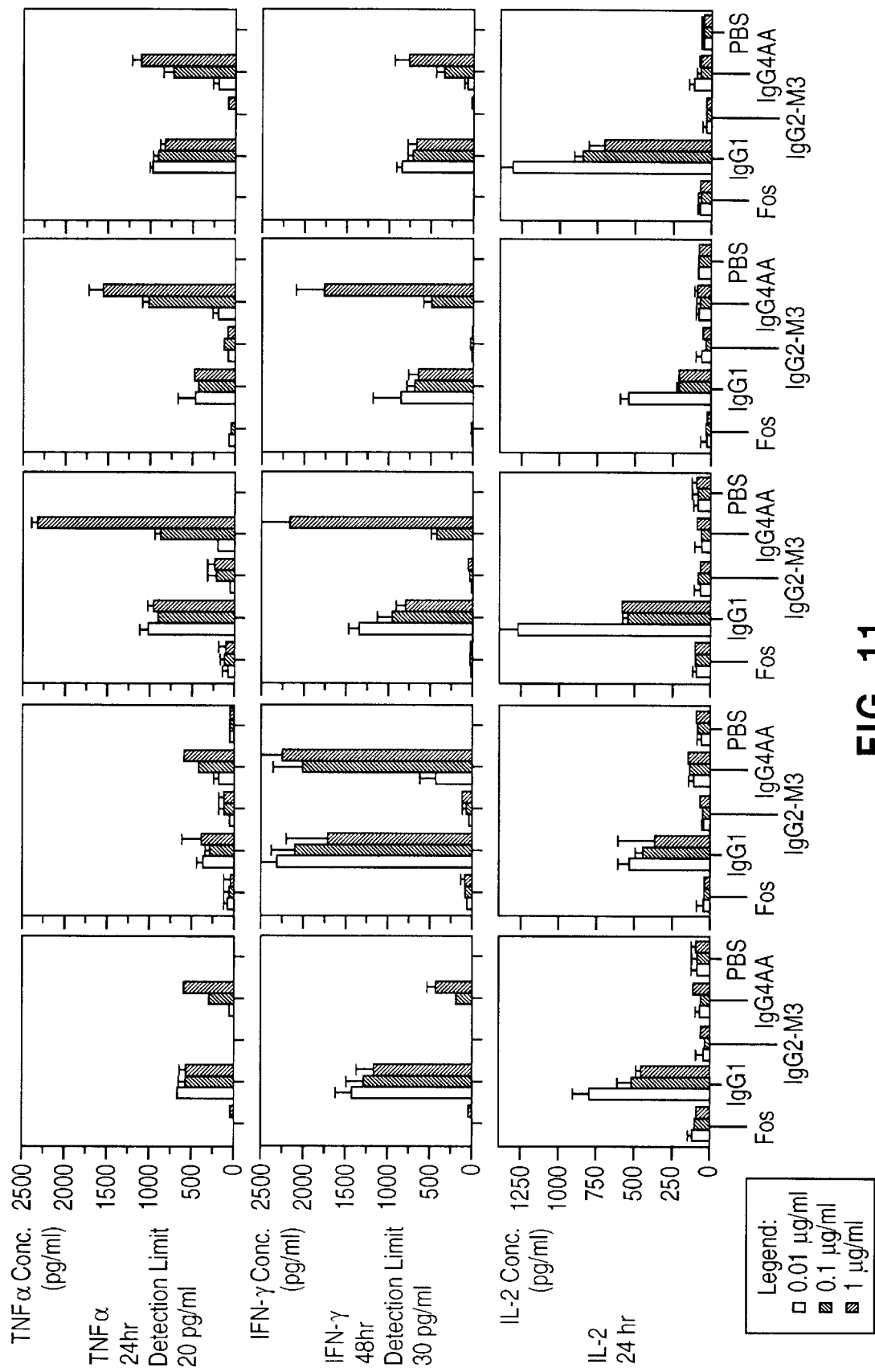

FIG. 11. Release of TNF-α, IFN-α and IL-2 induced by humanized M291 anti-CD3 antibodies. The assay was performed as in FIG. 8 with PBMCs from five human donors using the indicated antibody concentrations, and cytokine release measured at the indicated times.

DEFINITIONS

The term IgG2 constant region refers to the specific IgG2 constant region sequence described by Ellison & Hood, *Proc. Natl. Acad. Sci. USA* 79, 1984 (1981), allelic variants thereof, and other forms thereof bearing a high degree of sequence identity (e.g., at least 90, 95 or 99% sequence identity to the sequence of Ellison & Hood, supra).

Preferably, residue positions which are not identical differ by conservative amino acid substitutions. The term includes a full-length constant region and fragments thereof such as CH1, hinge, CH2, and CH3 regions and combinations thereof. IgG2 constant regions are found in humans and primates.

Percentage sequence identities are determined by the programs GAP or BESTFIT using default gap weights.

Amino acids in the constant region are numbered by alignment with the human antibody EU (see Cunningham et al., *J. Biol. Chem.*, 9, 3161 (1970)). That is, the heavy and light chains of an antibody are aligned with the heavy and light chains of EU to maximize amino acid sequence identity and each amino acid in the antibody is assigned the same number as the corresponding amino acid in EU. The EU numbering system is conventionally used in the art (see generally, Kabat et al, Sequences of Protein of Immunological Interest, NIH Publication No. 91-3242, US Department of Health and Human Services (1991)). According to this convention, the wildtype IgG2 constant region described by Ellison & Hood, supra, lacks an amino acid at position 236. Amino acids from the variable regions of the mature heavy and light chains of immunoglobulins are here designated Hx and Lx respectively, where x is a number designating the position in the variable region sequence.

Anti-CD3 antibodies of the invention show specific binding to the human CD3 antigen. Most antibodies to human CD3 do not crossreact with cognate antigens from lower mammals.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

From N-terminal to C-terminal, both light and heavy chains comprise the domains FR1, CDR1, FR2, CDR2, FR3, CDR3 and FR4. The assignment of amino acids to each domain is in accordance with the definitions of Kabat (1991), supra, and/or Chothia & Lesk, *J. Mol. Biol.* 196:901–917 (1987); Chothia et al., *Nature* 342:878–883 (1989).

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function. The variable regions of each light/heavy chain pair form the antibody binding site. Thus, an intact antibody has two binding sites.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7 (incorporated by reference in its entirety for all purposes)).

The term epitope includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

The term patient includes human and veterinary subjects.

A test antibody competes with a reference antibody for specific binding to an antigen when an excess of the test antibody substantially inhibits binding of the reference antibody to the antigen in a competition assay. Substantially inhibits means that the test antibody reduces specific binding of the reference usually by at least 19%, 25%, 50%, 75%, or 90%. A competing antibody binds to the same or similar epitope on an antigen as the reference antibody or to an epitope which is sufficiently proximal to the epitope bound by the reference antibody to inhibit binding of the reference antibody to the antigen.

DETAILED DESCRIPTION

The invention provides IgG2 constant regions mutated such that they substantially lose the capacity to specifically bind Fcγ receptors and thereby activate mitogenic responses in T-cells in most patients. The invention also provides novel humanized anti-CD3 antibodies derived from the mouse M291 antibody, into which the mutated IgG2 constant regions can be incorporated. The mutated IgG2 constant regions can also be incorporated into other anti-CD3 or other antibodies.

I. Mutation of IgG2 Constant Region

The invention provides IgG2 constant regions having mutations in the $C_H2$ region substantially lacking the capacity to interact with Fcγ receptors. The mutations associated with loss of Fcγ receptor binding occur within residues 234–237 of the IgG2 constant region with residues numbered by the EU convention. Mutations are selected according to several constraints. First, the mutations should cause loss of specific binding (i.e., $Ka<10^6$ $M^{-1}$) to the Fcγ receptor naturally recognized by IgG2 (FcRII) without causing concomitant acquisition of binding to other Fcγ receptors not naturally recognized by IgG2. In other words, mutated forms of IgG2 of the invention do not usually show specific binding to any of the Fcγ receptors, at least in the frequently occurring allelic forms. Substantial loss of binding to Fcγ receptors results in substantial loss of T-cell mitogenic activity.

Second, an anti-CD3 antibody incorporating a mutated IgG2 constant region should have substantially the same binding affinity and avidity for CD3 (e.g., within a factor of 3, 5, or 10-fold) as a second anti-CD3 antibody, which has a wildtype IgG2 constant region, but is otherwise identical. Nor should mutations affect the specificity of binding (e.g., an antibody bearing a mutated IgG2 constant region should compete for binding to human CD3 with an unmutated form of the antibody). Third, the mutation should not perturb the structure of the constant region so far from that of a natural constant region as to result in increased immunogenicity. Thus, antibodies bearing mutated constant regions of the invention remain useful for suppressing T-cell immune responses in therapeutic methods.

The isolation of five exemplary IgG2 constant regions containing different combinations of mutations satisfying these criteria is described below. In these constant regions, residues 234, 235 and 237, defined by the EU numbering system, form a segment of amino acids selected from the group consisting of:

ala ala gly,
val ala ala,
ala ala ala,
val glu ala, and
ala glu ala.

Position 236 is unoccupied in these mutant constant regions, as it is in a wildtype IgG2 constant region.

Equivalently, these mutant constant regions can be described as comprising one of the following nonnaturally occurring segment of amino acids between positions 234 and 237:

ala ala __ gly,
val ala __ ala,
ala ala __ ala,
val glu __ ala,
ala glu __ ala,
where __ represents the absence of an amino acid at position 236.

Although not all of the substitutions in these examples are conservative by the classification of amino acids described above, they do not introduce substantial changes in charge distribution or conformation of the IgG2 constant region containing them. Thus, Fcγ receptor binding and mitogenic activation of T-cells can be substantially reduced by relatively conservative modifications. Other mutations that may satisfy the criteria can be made by replacing the amino acids 234 through 237, separately or together, with any of the 20 usual amino acids, or deleting any of these amino acids.

The mutated IgG2 constant regions are incorporated into anti-CD3 antibodies by recombinant techniques. Fully human or humanized anti-CD3 antibodies are most suitable, for example, humanized M291 or humanized OKT3 (Allegre et al. (1992), supra). Antibodies incorporating these constant regions have desirable properties as immunosuppressive agents in that they can suppress immune responses of T-cells without inducing mitogenic activity resulting in harmful release of cytokines, at least in most (meaning at least 67%, 75%, 90% or 95% as used herein) patients. An anti-CD3 antibody incorporating the mutated IgG2 constant regions of the invention does not show significantly greater binding (e.g., more than 2, 5 or 10-fold) to Fcγ receptors than a F(ab')$_2$ fragment of the antibody (which completely lacks an Fcγ R binding domain). As a result of this loss of binding affinity, anti-CD3 antibodies incorporating mutated IgG2 constant regions do not stimulate significant proliferative activity in T cells relative to background levels. Further, anti-CD3 antibodies incorporating mutated IgG2 constant regions of the invention do not significantly stimulate release of cytokines, such as TNF-α, IL-2 or IFN-γ or induce expression of the IL-2 receptor by T cells bound by the antibodies relative to corresponding F(ab')$_2$ fragments. That is, in most patients or in vitro with cells from most donors, mitogenic activity (i.e., induced proliferation and/or cytokine release and/or receptor expression) is reduced by at least 2, 5, 10 or 100-fold from the corresponding activity observed with unmutated IgG1 and/or IgG2 anti-CD3 antibodies, and/or is within 2, 5, or 10-fold of that with F(ab')$_2$ fragments. Antibodies incorporating mutated IgG2 constant regions offer advantages over F(ab')$_2$ fragments of longer serum half-life. Antibodies incorporating mutated IgG2 regions also often show longer in vivo half-lives and reduced immunogenicity relative to antibodies having wild type constant regions presumably due to their inability to interact with Fcγ receptors.

II. Humanized Anti-CD3 Antibodies

The invention further provides novel humanized anti-CD3 antibodies derived from the mouse antibody M291 into which mutated IgG2 constant regions can be incorporated (see also U.S. Ser. No. 08/397,411 incorporated by reference in its entirety for all purposes). The humanized antibodies can also be used with other constant regions or as fragments lacking intact constant regions. The humanized forms of immunoglobulins have variable framework region(s) substantially from a human immunoglobulin (termed an acceptor immunoglobulin) and complementarity determining regions substantially from a mouse immunoglobulin (referred to as the donor immunoglobulin). The constant region(s), if present, are also substantially (e.g., 85%, 90%, 95% or higher) from a human immunoglobulin. The humanized antibodies exhibit a specific binding affinity for their respective antigens of at least $10^7$, $10^8$, $10^9$, or $10^{10}$ M$^{-1}$. Often the upper and lower limits of binding affinity of the humanized antibodies are within a factor of three or five or ten of that of the mouse antibody from which they were derived.

Having selected the CDR and framework components of humanized immunoglobulins, a variety of methods are available for producing such immunoglobulins. Because of the degeneracy of the code, a variety of nucleic acid sequences encode each immunoglobulin amino acid sequence. The desired nucleic acid sequences can be produced by de novo solid-phase DNA synthesis or by PCR mutagenesis of an earlier prepared variant of the desired polynucleotide. All nucleic acids encoding the antibodies described in this application are expressly included in the invention.

The variable segments of humanized antibodies as described supra are typically linked to mutated IgG2 constant regions as described above. However, other constant regions can also be employed, including IgM, IgG, IgD, IgA and IgE, and any isotype, including IgG1, natural IgG2, IgG3 and IgG4. When it is desired that the humanized antibody exhibit cytotoxic activity, the constant domain is usually a complement-fixing constant domain and the class is typically IgG$_1$. When such cytotoxic activity is not desirable, the constant domain may be of the IgG2 or IgG4 class. The humanized antibody can comprise sequences from more than one class or isotype. Human constant region DNA sequences can be isolated in accordance with well-known procedures from a variety of human cells, but preferably immortalized B-cells (see Kabat et al., supra, and WO87/02671). Ordinarily, the antibody contains both light chain and heavy chain constant regions. The heavy chain constant region usually includes CH1, hinge, CH2, CH3, and, sometimes, CH4 regions.

In another aspect, the invention encompasses DNA segments that encode the disclosed antibodies and constant regions. Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence (see Queen et al., *Proc. Natl. Acad. Sci. USA* 86, 10029 (1989); WO 90/07861; Co et al., *J. Immunol.* 148, 1149 (1992), *Antibody Engineering, A Practical Guide* (Borrebaeck, Ed., Freeman, N.Y. 1992)) which are incorporated herein by reference in their entirety for all purposes).

*E. coli* is one prokaryotic host useful particularly for cloning and/or expressing DNA sequences of the present invention. Other microbial hosts suitable for use include bacilli, such as *Bacillus subtilis*, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters can be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation.

Other microbes, such as yeast, can also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

Plants and plant cell cultures can be used for expression of the humanized immunoglobulins of the invention. (Larrick & Fry, Hum. *Antibodies Hybridomas* 2(4):172–89 (1991); Benvenuto et al., *Plant Mol. Biol.* 17(4):865–74 (1991); Durin et al., *Plant Mol. Biol.* 15(2):281–93 (1990); Hiatt et al., *Nature* 342:76–8 (1989), incorporated herein by reference in their entirety for all purposes). Preferable plant hosts include, for example: Arabidopsis, *Nicotiana tabacum*, *Nicotiana rustica*, and *Solanum tuberosum*. A preferred expression cassette for expressing polynucleotide sequences encoding the humanized anti-CD3 antibodies of the invention is the plasmid pMOG18 in which the inserted polynucleotide sequence encoding the humanized immunoglobulin chain is operably linked to a CaMV 35S promoter with a duplicated enhancer; pMOG18 is used according to the method of Sijmons et al., *Bio/Technology* 8:217–221 (1990), incorporated herein by reference in its entirety for all purposes. Alternatively, a preferred embodiment for the expression of humanized immunoglobulins in plants follows the methods of Hiatt et al., supra, with the substitution of polynucleotide sequences encoding the humanized anti-CD3 antibodies of the invention for the immunoglobulin sequences used by Hiatt et al., supra. *Agrobacterium tumifaciens* T-DNA-based vectors can also be used for expressing humanized immunoglobulin sequences, preferably such vectors include a marker gene encoding spectinomycin-resistance or other selectable marker.

Insect cell culture can also be used to produce the humanized immunoglobulins of the invention, typically using a baculovirus-based expression system. The humanized immunoglobulins can be produced by expressing polynucleotide sequences encoding the humanized immunoglobulins according to the methods of Putlitz et al., *Bio/Technology* 8:651–654 (1990), incorporated herein by reference in its entirety for all purposes. The method of Putlitz et al. can be followed with the modification that polynucleotide sequences encoding the humanized anti-CD3 antibodies of the invention are inserted in place of the mouse monoclonal Ab 6A4 heavy chain and light chain cDNA sequences of Putlitz et al.

In addition to microorganisms and plants, mammalian tissue cell culture can also be used to express and produce the polypeptides of the present invention (see Winnacker, *From Genes to Clones* (VCH Publishers, NY, 1987), which is incorporated herein by reference in its entirety for all purposes). Mammalian cells are actually preferred, because a number of suitable host cell lines capable of secreting intact immunoglobulins have been developed in the art, and include the CHO cell lines, various COS cell lines, HeLa cells, preferably myeloma cell lines, etc., or transformed B-cells or hybridomas. Expression vectors for these cells can include expression control sequences, such as an origin of replication, a promoter, an enhancer (Queen et al., *Immunol. Rev.* 89:49–68 (1986), which is incorporated herein by reference in its entirety for all purposes), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like. Generally, a selectable marker, such as a neo$^R$ expression cassette, is included in the expression vector.

The antibodies of the invention include fragments as well as intact antibodies. Typically, these fragments compete with the intact antibody from which they were derived for antigen binding. The fragments typically bind with an affinity of at least $10^7$ M$^{-1}$, and more typically $10^8$ or $10^9$ M$^{-1}$ (i.e., within the same ranges as the intact antibody). Humanized antibody fragments include separate heavy chains, Fab, Fab', F(ab')$_2$, and Fv and single-chain antibodies. Fragments are produced by recombinant DNA techniques, or by enzymic or chemical separation of intact immunoglobulins.

III. Human Antibodies

The mutated IgG2 constant regions of the invention can also be joined to the variable domains of fully human antibodies to CD3 by recombinant expression techniques. Human antibodies are produced by a variety of techniques described below. Some human antibodies are selected by competitive binding experiments, or otherwise, to have the same, or overlapping, epitope specificity as a particular mouse antibody, such as M291 or OKT3.

a. Trioma Methodology

The basic approach and an exemplary cell fusion partner, SPAZ-4, for use in this approach have been described by Oestberg et al., *Hybridoma* 2:361–367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells—two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte resulting in an antibody-producing trioma cell line.

The immunized B-lymphocytes are obtained from the blood, spleen, lymph nodes or bone marrow of a human donor. In vivo immunization of a living human with human T-cells or CD3 is usually undesirable because of the risk of initiating a harmful response. Thus, B-lymphocytes are usually immunized in vitro with T-cells, purified CD3 or an antigenic fragment thereof. The human form of CD3 is preferably used. B-lymphocytes are typically exposed to antigen for a period of 7–14 days in a medium such as RPMI-1640 (see Engleman, supra) supplemented with 10% human plasma.

The immunized B-lymphocytes are fused to a xenogeneic hybrid cell such as SPAZ-4 by well known methods. For example, the cells are treated with 40–50% polyethylene glycol of MW 1000–4000, at about 37° C., for about 5–10 min. Cells are separated from the fusion mixture and propagated in medium selective for the desired hybrids (e.g., HAT or AH). Clones secreting antibodies having the required binding specificity are identified by assaying the trioma culture medium for the ability to bind to CD3 or a fragment thereof. Triomas producing human antibodies having the desired specificity are subcloned by the limiting dilution technique and grown in vitro in culture medium. The trioma cell lines obtained are then tested for the ability to bind CD3 or a fragment thereof.

Although triomas are genetically stable they do not produce antibodies at very high levels. Expression levels can be increased by cloning antibody genes from the trioma into one or more expression vectors, and transforming the vector into a cell line such as the cell lines discussed supra for expression of recombinant or humanized immunoglobulins.

b. Transgenic Non-Human Mammals

Human antibodies against CD3 can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO 93/12227 (1993); Kucherlapati, WO 91/10741 (1991) (each of which is incorporated by reference in its entirety for all purposes). Transgenic mice are particularly suitable. Anti-CD3 antibodies can be obtained by immunizing a transgenic nonhuman mammal, such as described by Lonberg or Kucherlapati, supra, with T-cells, CD3 or an antigenic fragment thereof. Monoclonal antibodies are prepared by, e.g., fusing B cells from such mammals to suitable myeloma cell lines using conventional Kohler-Milstein technology.

c. Phage Display Methods

A further approach for obtaining human anti-CD3 antibodies is to screen a DNA library from human B cells according to the general protocol outlined by Huse et al., *Science* 246:1275–1281 (1989). Antibodies binding to CD3 or a fragment thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to CD3 or fragment thereof.

In a variation of the phage-display method, human antibodies having the binding specificity of a selected murine antibody can be produced. See Winter, WO 92/20791. In this method, either the heavy or light chain variable region of the selected murine antibody (e.g., M291) is used as a starting material. If, for example, a light chain variable region is selected as the starting material, a phage library is constructed in which members displays the same light chain variable region (i.e., the murine starting material) and a different heavy chain variable region. The heavy chain variable regions are obtained from a library of rearranged human heavy chain variable regions. A phage showing strong specific binding for CD3 (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for CD3 are selected. These phage display the variable regions of completely human anti-CD3 antibodies. These antibodies usually have the same or similar epitope specificity as the murine starting material (e.g., M291).

IV. Therapeutic Methods

Pharmaceutical compositions comprising antibodies of the present invention are useful for parenteral administration, i.e., subcutaneously, intramuscularly and particularly, intravenously, to patients suffering from, at or risk of, conditions manifesting undesired immune responses. Such conditions include autoimmune diseases, transplant rejection (particularly, following heart, lung, kidney or liver transplants), graft vs. host disease (following bone marrow transplants), inflammation, allergic reactions, and sepsis. Exemplary autoimmune diseases are rheumatoid arthritis, multiple sclerosis, type I diabetes, system lupus erythematosus and inflammatory bowel disease. The pharmaceutical compositions are particularly useful for treatment of acute flares or exacerbations of these or other autoimmune diseases.

The compositions for parenteral administration commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. The compositions can contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate. The concentration of the antibodies in these formulations can vary widely, i.e., from less than about 0.01%, usually at least about 0.1% to as much as 5% by weight and are selected primarily based on fluid volumes, and viscosities in accordance with the particular mode of administration selected.

A typical composition for intravenous infusion can be made up to contain 250 ml of sterile Ringer's solution, and 10 mg to 100 mg of antibody. See *Remington's Pharmaceutical Science* (15th Ed., Mack Publishing Company, Easton, Pa., 1980).

The compositions containing the present antibodies can be administered for prophylactic and/or therapeutic treatments. In therapeutic application, compositions are administered to a patient already affected in an amount sufficient to cure or at least partially arrest the condition and its complications. An amount adequate to accomplish this is defined as a "therapeutically effective dose". Amounts effective for this use depend upon the severity of the condition and the general state of the patient's own immune system, but generally range from about 0.01 to about 100 mg of antibody per dose, with dosages of from 0.1 to 50 mg and 1 to 10 mg per patient being more commonly used. Single or multiple administrations on a daily, weekly or monthly schedule can be carried out with dose levels and pattern being selected by the treating physician.

In prophylactic applications, compositions containing the antibodies are administered to a patient who is at risk of developing the disease state to enhance the patient's resistance. Such an amount is defined to be a "prophylactically effective dose". In this use, the precise amounts again depend upon the patient's state of health and general level of immunity, but generally range from 0.1 to 100 mg per dose, especially 1 to 10 mg per patient.

IV. Diagnostic Methods

The M291 antibody (both mouse and humanized forms) is also useful in diagnostic methods in immunological monitoring of patients infected with pathogenic organisms (e.g., in determining the T-cell count of AIDS patients) or in patients having disorders of the immune system. Methods of diagnosis can be performed in vitro using a cellular sample (e.g., blood sample, lymph node biopsy or tissue) from a patient or can be performed by in vivo imaging. The M291 antibody can also be used for research purposes in classifying leukocyte subtypes, e.g., as part of an antibody panel. For such purposes, M291 is preferably used in an ELISA, RIA or other art-known assay format.

EXAMPLES

1. Materials and Methods a. Cloning of V region cDNAs

The V domain cDNAs for the H and L chains of OKT3 were cloned by an anchored PCR (polymerase chain reaction) method described by Co et al., *J. Immunol.* 148, 1149 (1992) from hybridoma cells expressing OKT3 (ATCC CRL 8001). Amplification was performed on cDNA using 3' primers that anneal respectively to the C region of the mouse gamma chain and kappa chain, and a 5' primer that anneals to the added G-tail of the cDNA. The VH and the VL cDNAs were subcloned into a pUC19 vector for sequence determination. Their sequences were identical to those published by Woodle et al. (see Woodle et al., *J. Immunol.* 148, 2756 (1992)).

b. Expression of chimeric anti-CD3 antibodies The $V_H$ and $V_L$ cDNAs of OKT3 were made into exons including signal sequences, J segments and splice donor sequences; and were surrounded by XbaI sites (see Co et al., *J. Immunol.* 148, 1149 (1992)). The $V_L$ sequence was inserted at the XbaI site of an expression vector pvk.rg, and the $V_H$ sequence similarly inserted in various heavy chain expression vectors, an example of which is pVg2.D.Tt. The vector pVk.rg is similar to pVk (Co et al., ibid.) except the orientation of the gpt unit has been reversed. The vector pVg2.D.T.t is similar to pVg1 (Co et al., ibid.) but contains a genomic fragment including the γ2 constant region (Ellison & Hood, Op. Cit.) instead of γ1, and contains the transcriptional terminator (Tt) of the human complement gene C2 (+37 to +162 bp from the C2 poly A site; see Ashfield et al., *EMBO J.* 10, 4197 (1991)). The various human heavy chain vectors differ only in the Fc-coding sequences. For coexpression of heavy and light chains in one plasmid, an EcoRI fragment containing the hCMV promoter, the entire heavy chain gene, the polyA signal, and the transcription termination signal was taken from the heavy chain expression vector; and cloned into the unique EcoRI site of the light chain expression plasmid has both the heavy and (FIG. 2). Each resulting plasmid has both the heavy and light chains encoded in one vector. Due to the presence of the transcription termination signal (Tt) situated between them, the two genes are transcribed independently by hCMV promoters (see Boshart et al., *Cell* 41, 521, (1985)). In one case, only the $C_H 1$ exons and hinge of the human γ1 constant region gene were included and the hinge exon was fused with DNA encoding the leucine zipper Fos to make a chimeric F(ab')$_2$ Fos (see Tso et al., *J. Hematother.* 4, 389 (1995)). For expression of a particular antibody, the corresponding plasmid was transfected into the mouse myeloma cell line TSB by electroporation. TSB cells are derived from mouse myeloma NSB cells (ECACC 85110503) by selecting for ability to grow in serum-free medium according to the procedure of Sato et al (see Sato et al., *J. Exp. Med.* 165, 1761 (1987)). The cells from each transfection were selected for gpt expression. Transfectants were grown in serum-free medium, and antibodies were purified from spent cultures by protein G affinity chromatography.

c. Mutagenesis of γ2 and γ4 $C_H 2$ exons

A PCR procedure was used to introduce mutations into the $C_H 2$ regions of γ2 and γ4 exons. For each mutagenesis, two complementary primers containing the mutated sequence were synthesized. One of these was used with an upstream primer to synthesize by PCR reaction the 5' portion, and the other with a downstream primer to synthesize the 3' portion of the desired fragment. Wild type Fc sequences were used as templates. The two PCR products were then mixed, annealed and amplified again using the upstream and downstream primers. For γ2 mutagenesis, the upstream primer used was 5' G G A C A C C T T C T C T C C T C C C (SEQ ID NO:10), and the downstream primer was 5' C C C A A G C T T G G G T G G G C C G A G C C G G C C T C T G T C C (SEQ ID NO:11). These primers respectively flank the hinge exon and the $C_H 2$ exon. The two complementary primers for mutant 1 were 5' G C A C C A C C T G C G G C A G G A C C G T C A (SEQ ID NO:12), and 5' T G A C G G T C C T G C C G C A G G T G G T G C (SEQ ID NO:13). Complementary primers for all other IgG2 mutants were similar except for the mutated codons. The amplification reaction product was cut with PstI and SfiI, two restriction sites that flank the hinge and the $C_H 2$ exons, and the resulting 525 bp fragment was introduced into the IgG2 expression vector between PstI and SfiI sites. Similarly, a mutagenized 241 bp PstI-PmlI fragment was generated for the $C_H 2$ exon of γ4, and was introduced into the IgG4 expression vector. Sequence analysis was performed for each expression vector to ensure only the desired mutations were introduced.

d. T cell proliferation assay

Peripheral Blood Mononuclear Cells (PBMCs) in RPMI plus 10% FCS were plated at $2 \times 10^5$ cells per well in a 96-well microtiter plate. Antibodies at various concentrations were added, and the cells were incubated at 37° C. for 3 days. [$^3$H]-Thymidine was added at 1 μCi per well, and the plates were incubated for an additional 12 hr before harvesting. Cells were harvested on a cell harvester, and [$^3$H]-thymidine incorporation was measured in a liquid scintillation counter. All data were expressed as the mean of triplicate determinations.

e. FcRII-dependent T cell retargeting assay

Activated human T cells were obtained by incubating PBMC with phytohemagglutinin (PHA) for three days in RPMI medium supplemented with 10% FCS at 37° C. followed by passage in medium containing IL-2 for 5 days. K562 cells, which express FcRII, were labeled with $^{51}$Cr by adding 100 μCi of $^{51}$Cr to $5 \times 10^6$ target cells in 1 ml of RPMI medium. After 1 hour incubation at 37° C., the cells were washed twice. T cells (50 ml) and labeled K562 target cells ($7 \times 10^4$ in 50 ml) at an effector:target ratio of 25:1 were plated in U-bottom microtiter plates. Chimeric anti-CD3 antibody at the desired concentration was then added. All samples were plated in triplicate. Plates were centrifuged, incubated for 4 hr at 37° C., and centrifuged again. Cell lysis was measured by determining the amount of $^{51}$Cr released into 100 μl of cell free supernatant from each sample. Counting was done in a Beckman model 5500 gamma counter. The percentage of specific lysis was determined by the following equation: $(E-S/M-S) \times 100$, where E is the average of triplicate sample counts per minute for sample, S is the spontaneous release in sample with target cells only, and M is the maximal release for samples with target cells and 100 μl of 1% SDS.

f. Competition assay to compare the relative avidity of chimeric OKT3 antibodies for the CD3 antigen Human T cells were resuspended in complete RPMI medium at $2.5 \times 10^6$ cells/ml. Dilutions of the test (chimeric OKT3) antibodies or control (murine OKT3) antibody were added and incubated at 4° C. for 1 hr. A fixed, subsaturating amount of FITC-conjugated murine OKT3 was added, and the cells were incubated at 4° C. for 1 hr, washed, and resuspended in 1% paraformaldehyde. The cells were then analyzed using flow cytometry. Each sample's fluorescence intensity was compared to that of the control without any competitive antibody. Values are expressed in percent of control fluorescence intensity.

g. Anti-CD3-mediated cytokine release and CD25 expression

PBMCs and antibodies were plated as in the T cell proliferation assay. Samples were taken at 24 hr for TNF-α and IL-2 determination, and at 72 hr for IFN-γ determinations. Commercial assay kits were used to determine the levels of TNF-α and IFN-γ in the medium. The levels of IL-2 were determined by a proliferation assay using an IL-2 dependent cell line HT-2. The percentage of T cells expressing the activation marker IL-2 receptor-α (CD25) at 90 hr was measured using a two-color FACS assay. A humanized, FITC-conjugated anti-Tac antibody was used to label the activation marker CD25 on the T cell surface, and a mouse anti-human CD7 antibody in conjunction with PE-conjugated goat anti-mouse IgG was used to label total T cells. The ratio of the two cell numbers is expressed as percentage of T cells that are CD25 positive.

2. Results a. Mutations in the $C_H2$ region of IgG2

The sequences of all wildtype IgG isotypes in the CH2 region are shown in FIG. 3. IgG1 and IgG3 have the identical sequence, Leu-Leu-Gly-Gly, in this region; and IgG4 differs only in having a Phe residue at position 234. IgG2, however, has a very different sequence in this region. In addition to lacking an amino acid at position 236, it differs from the sequences of IgG1, IgG3 and IgG4 in two of the remaining three positions (234 and 235). The unique sequence, Val Ala__Gly, of IgG2 may account for its specificity for FcRII only.

Mutations were introduced, either one at time, or in combinations, to cover all residues in this region. The sequences at position 234–237 of five IgG2 Fc variants generated are shown in FIG. 3. The first three mutants were Ala scanning mutations. No change was made at position 235 because it is already an Ala residue. In mutants 4 and 5, position 235 was also changed to a Glu residue. Anti-CD3 of the mouse IgG2b isotype, which is not mitogenic, has a Glu residue at this position. For comparison, a mutant containing two Ala substitutions at positions 234 and 235 of IgG4 was made (see Alegre et al., *Transplantation,* 57, 1537 (1994)). The entire sequence of the IgG2 mutant 3's heavy chain constant region is shown in FIG. 4.

The five IgG2 mutant constant regions were incorporated into chimeric OKT3 antibodies by combining with the OKT3 variable region, as was an IgG4 variant with two Ala substitutions at positions 234 and 235, and all natural human IgG isotypes. In addition a chimeric OKT3 F(ab')$_2$ derived from IgG1 was made by the leucine zipper technique (see Kostelny et al., *J. Immunol*, 148, 1547 (1992)). The recombinant F(ab')$_2$ is entirely Fc-less. All of these OKT3 chimeric antibodies and fragments were tested for T cell proliferation in a mitogenic assay using human PBMC from eight donors. Multiple donors were used because their PBMCs may respond to anti-CD3 differently due to polymorphism of the Fc receptors. A useful anti-CD3 variant should preferably be nonmitogenic to T cells from most or all donors. Different concentrations of the antibodies were also used to ensure T cell activation does not occur in the clinically relevant dose range.

b. Reduced mitogenic activity in anti-CD3 IgG2 mutants

Results of the T cell proliferation assay are shown in FIG. 5. Anti-CD3 antibodies of the IgG1 and IgG4 isotype were mitogenic in most donors tested, and there were variations in the donors' responses to anti-CD3 of the IgG2 and IgG3 isotypes. All five IgG2 mutants had attenuated mitogenic activities in PBMCs whereas wild type IgG2 gave significant proliferation. Mutants 2–5 induced the least proliferation. For most donor samples, the mitogenic activities of mutants 2–5 were as low as that of the Fc-less F(ab')$_2$ and less mitogenic than the IgG4 mutant. Only in one donor (D), at high antibody concentrations (1 μg/ml), was notable proliferation observed for these mutants, but this was not associated with cytokine release or induction of the T cell activation marker CD25. Mutants 2–5 thus have the attributes of an nonactivating antibody. In particular, they induce much less proliferation than the IgG4 mutant, which was comparable to IgG1 and unmutated IgG4 at the high (1 μg/ml) concentration.

c. Anti-CD3 IgG2 mutant 3 does not mediate retargeting that is dependent on the interaction of Fc and FcRII Fc receptor-bearing cells and T cells can be bridged by anti-CD3 antibody if it has a functional Fc. Such bridging can trigger T cells to lyse the Fc receptor-bearing cells (reverse lysis), providing a sensitive assay to probe for the interaction of the anti-CD3 IgG2 mutant and the Fc-receptors. Mutant 3 was picked as a representative of the IgG2 mutants in this assay. Since IgG2 interacts mainly with FcRII, K562 cells, which express FcRII on their surface, were used as the target cells for the IgG2 mutant 3-mediated reverse lysis. The data are shown in FIG. 6. Anti-CD3 IgG2 mutant 3 was as inert as the F(ab')$_2$ form of the antibody in mediating the reverse lysis, whereas the wild type IgG2 could mediate up to 32% specific lysis of K562 cells. Although the activity of the IgG1 isotype was low due to its low affinity for FCRII, it could still mediate lysis equivalent to the IgG2 level at high antibody concentrations. In a separate experiment, anti-CD3 IgG2 and mutant 3 were both ineffective in mediating FcRI-dependent reverse lysis. Mutations introduced at the Fc of IgG2 mutant 3, therefore, did not reverse the poor affinity of IgG2 for FcRI. These experiments confirmed that mutant 3 has very low affinity for FcRI and FcRII.

d. The avidity of chimeric anti-CD3 for its antigen was not substantially affected by its isotype or Fc mutations The relative avidity of murine OKT3, chimeric OKT3 F(ab')$_2$, IgG1, IgG2 and IgG2 mutant 3 for T cells was evaluated using the competition assay described above to eliminate the possibility that the lack of T cell activation or FcRII-mediated reverse lysis by OKT3 IgG2 mutant 3 is due to its lack of binding to the T cells. Chimeric OKT3 IgG1 blocked the binding of FITC-labeled murine OKT3 as well as the unlabeled OKT3 (FIG. 7). This antibody, therefore, must have an avidity very similar to that of the murine OKT3. Chimeric OKT3 IgG2 and IgG2 mutant 3, were slightly less efficient in blocking the binding of FITC-labeled murine OKT3 than unlabeled OKT3. Their avidity was estimated to be within 2 to 3-fold compared to that of the chimeric IgG1. This experiment, therefore, demonstrated that the antigen binding activity of IgG2 and its mutant was substantially retained. Since wild type IgG2 with similar avidity was capable of activating T cells in PBMCs from appropriate donors, such slight reduction in avidity is not sufficient to account for the lack of activity in mutant 3.

e. Anti-CD3 IgG2 mutant 3 does not induce cytokine release

Next the capacity of IgG2 mutants to induce cytokine release and to up-regulate IL-2 receptors in T cells was tested. PBMCs from six of the eight donors tested previously were plated with different concentrations of chimeric OKT3 F(ab')$_2$ and chimeric OKT3 of the isotypes IgG1, IgG2, and IgG2 mutant 3; and the supernatants were tested for activation markers TNF-α and IL-2 at 24 hr; and IFN-γ at 72 hr. In addition, T cells were assayed for the activation marker IL-2 receptor-α (CD25) at 90 hr. The results are shown in FIGS. 8 and 9. As expected, IgG1 was most active in releasing the three cytokines and inducing CD25 expression. There was also measurable induction of CD25 and cytokine release with IgG2 in all six donors. IgG2 mutant 3, on the other hand, was the least activating among the three antibodies tested. In all cases these activation markers were barely detectable above background. Even in donor D where some proliferation was previously observed at high concentration (1 μg/ml) of IgG2 mutant 3 (FIG. 5), the expression of these activation markers was negligible. Based on these assays, anti-CD3 IgG2 mutant 3 appeared to have minimal effects in T cell activation and would be the safest among all antibodies tested in these experiments.

3. Construction of humanized M291 antibody a. Cloning and sequencing of mouse M291 variable region cDNAs Mouse M291 heavy and light chain variable region cDNAs were cloned from mRNA isolated from hybridoma cells using anchored PCR (Co et al., *J. Immunol.* 148:1149 (1992)). The 5' primers used annealed to poly-dG tails added to the cDNA, and the 3' primers to the constant regions. The amplified DNA fragments were then inserted into pUC19, and several heavy and light chain clones were sequenced and respectively found to be the same. These variable region cDNA sequences and the amino acid sequences derived from them are shown in FIGS. 1A and B.

b. Design of humanized M291 variable regions

To retain the binding affinity of the mouse antibody in the humanized antibody, the general procedures of Queen et al. were followed (Queen et al. *Proc. Natl. Acad. Sci. USA* 86:10029 (1989) and WO 90/07861). The choice of framework residues can be critical in retaining high binding affinity. In principle, a framework sequence from any human antibody can serve as the template for CDR grafting; however, it has been demonstrated that straight CDR replacement into such a framework can lead to significant loss of binding affinity to the antigen (Glaser et al., *J. Immunol.* 149:2606 (1992); Tempest et al., Biotechnology 9:266 (1992); Shalaby et al., *J. Exp. Med.* 17:217 (1992)). The more homologous a human antibody is to the original murine antibody, the less likely that the human framework introduces distortions into the mouse CDRs that could reduce affinity. Based on a sequence homology search against an antibody sequence database, the human antibody HF2-1/17 provides good framework homology to the mouse M291 light chain variable region, and the human antibody 21/28 provides good framework homology to the mouse M291 heavy chain variable region, although other highly homologous human antibodies would be suitable as well, especially kappa light chains from human subgroup I or heavy chains from human subgroup I (as defined by Kabat et al., op. cit.).

The computer program ENCAD (Levitt et al., *J. Mol. Biol.* 168:595 (1983)) was used to construct a molecular model of the M291 variable domain, which was used to locate the amino acids in the M291 framework that were close enough to the CDRs to potentially interact with them. To design the humanized M291 light and heavy chain variable regions, the CDRs from the mouse M291 antibody were grafted respectively into the framework regions of the human HF2-1/17 and 21/28 antibody light and heavy chains. At framework positions where the computer model suggested significant contact with the CDRs, the amino acids from the mouse antibody were substituted for the original human framework amino acids. For humanized M291, this was done at residues 30, 67, 68, 70, 72 and 74 of the heavy chain and at no residues of the light chain. Also, framework residues that occurred only rarely at their positions in the database of human antibodies were replaced by a human consensus amino acid at those positions. For humanized M291 this was done at residue 44 of the heavy chain.

The final sequence of the humanized M291 antibody (HuM291) light and heavy chain variable regions is shown in FIGS. 1C and D. However, many of the potential CDR-contact residues are amenable to substitutions of other amino acids that may still allow the antibody to retain substantial affinity to the antigen. The following table lists a number of positions in the framework where alternative amino acids may be suitable (LC=light chain, HC=heavy chain):

| Position | HuM291 | Alternatives |
| --- | --- | --- |
| LC-69 | D | E, S |
| HC-30 | I | T, V, L |
| HC-44 | G | R |
| HC-67 | K | R |
| HC-68 | A | V |
| HC-70 | L | I, V |
| HC-72 | A | R |

Likewise, many of the framework residues not in contact with the CDRs in the humanized M291 variable domain can accommodate substitutions of amino acids from the corresponding positions of the human HF2-1/17 and 21/28 antibodies, from other human antibodies, from the mouse M291 antibody, or from other mouse antibodies, without significant loss of the affinity or non-immunogenicity of the humanized antibody. The following table lists a number of additional positions in the framework where alternative amino acids may be suitable:

| Position | HuM291 | Alternatives |
| --- | --- | --- |
| LC-3 | Q | V |
| LC-4 | M | L |
| HC-1 | Q | E |
| HC-75 | S | A, T |
| HC-81 | M | I, L, V |

Selection of combinations of alternative amino acids might be used to produce versions of humanized M291 that have varying combinations of affinity, specificity, non-immunogenicity, ease of manufacture, and other desirable properties. Thus, the examples in the above tables are offered by way of illustration, not of limitation.

C. Construction of humanized M291

Once the humanized variable region amino acid sequences had been designed as described above, DNA segments were constructed to encode them, including signal peptides, splice donor signals and appropriate restriction sites. Each variable region coding segment was constructed and amplified using ten overlapping synthetic oligonucleotides in four steps: (1) the four central pairs of overlapping oligonucleotides were denatured, allowed to anneal, and extended with the Klenow fragment of DNA polymerase to produce four longer overlapping oligonucleotides from eight shorter ones; (2) these four oligonucleotides were denatured and then similarly combined to form two overlapping fragments of DNA; (3) the resulting pair of oligonucleotides were likewise joined to form the central portion of the coding segment; and (4) the final two flanking oligonucleotides, each containing an XbaI restriction site, were used in PCR to complete and the amplify the coding segments.

The humanized variable region coding segments were inserted into human expression vectors containing either the human $C_K$ coding segment or the human $C\gamma_2$ mutant 3 coding segment or the human $C\gamma_1$ coding segment, namely respectively pVk.rg and pVg2.D.Tt as described above, or the analogous vector pVg1.D.Tt. The light and each heavy chain coding segments were then respectively put into one expression vector as described (see FIG. 2). The two expression plasmids were linearized with FspI in preparation for transfection. Approximately 20 μg of each plasmid was separately transfected into 1×10⁷ TSO cells using a Gene Pulser apparatus (Bio-Rad) with two pulses at 1500 V and 3 μF according to the manufacturer's instructions. The cells were plated in a 96-well tissue culture plate, and after two days, selection medium (DMEM, 10% FCS, 1×penicillin-streptomycin (P/S) (Gibco), 1×HT supplement (Sigma), 0.25 mg/ml xanthine, 1 μg/ml mycophenolic acid) was applied.

After approximately two weeks, the clones that appeared were screened for antibody production by ELISA. Antibodies from a high-producing IgG1 clone and a IgG2 mutant 3 clone were prepared by growing the cells to confluency in serum-free medium and culturing until the cells died. The culture supernatant was run over a protein G-Sepharose column (Pharmacia); antibody was eluted with 0.1M glycine-HCl, 100 mM NaCl, pH 2.5 and subsequently dialyzed against phosphate-buffered saline (PBS). The purity of the antibody was verified by running it on an acrylamide gel and its concentration was determined by an $OD_{280}$ reading, assuming 1.3 mg of antibody protein has an $OD_{280}$ reading of 1.0.

d. Properties of humanized M291

To assess the ability of the humanized M291 antibodies to compete with the mouse M291 antibody for binding to CD3, and thereby measure their binding affinity, increasing concentrations of the antibodies were respectively mixed with 12.5 ng of tracer $^{125}$I-labelled murine antibody and incubated with 4×10⁵ IL-2-activated human T cells in 0.2 ml of binding buffer (PBS with 2% fetal calf serum, 0.1% sodium azide) for 90 min on ice. The cells were washed and centrifuged, and their radioactivities measured. The ratio of bound and free antibody were calculated. The binding affinities were calculated according to the methods of Berzofsky and Berkower (J. A. Berzofsky and I. J. Berkower, in Fundamental Immunology, W. E. Paul, ed., Raven Press, N.Y., 1984). The mouse M291 and the IgG1 M291 antibody competed with equal efficiencies (FIG. 10) and had the very high calculated affinities of $K_a=1.6\times10^9M^{-1}$, so the humanization procedure did not significantly alter the binding affinity of the original antibody. The humanized IgG2 Mutant 3 (IgG2M3) antibody competed slightly less well, perhaps because of greater rigidity of the IgG2 hinge region, but still had the high affinity of $K_a=5\times10^8M^{-1}$.

The ability of the humanized m291 IgG2M3 antibody to induce T-cell proliferation and lymphokine release using PBMCs from various donors was assessed in experiments analogous to the ones described above for the chimeric OKT3 IgG2 mutants. Like those mutants, the humanized M291 IgG2M3 antibody induced less proliferation and no or reduced release of the cytokines IFN-γ and TNF-α and IL-2 from most or all donors (FIG. 11).

All publications and patent applications cited above are herein incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A mutated IgG2 constant region comprising a nonnaturally occurring segment of amino acids between residues 234 and 237 defined by the EU numbering system, wherein an antibody comprising the variable region of an anti-CD3 antibody linked to the mutated IgG2 constant region induces a reduced mitogenic response in human T cells relative to a second antibody comprising the variable region of the anti-CD3 antibody linked to a natural IgG2 constant region.

2. A mutated IgG2 constant region, wherein residues 234, 235 and 237, defined by the EU numbering system, form a segment of amino acids selected from the group consisting of:

---
ala ala gly,
val ala ala,
ala ala ala,
val glu ala, and
ala glu ala.
---

3. The mutated IgG2 constant region of claim 2, wherein the segment is ala ala ala.

4. The mutated IgG2 constant region of claim 3, wherein the segment is contained within an otherwise naturally occurring human IgG2 constant region.

5. The mutated IgG2 constant region of claim 2 that comprises at least CH1, hinge, CH2, and CH3 regions.

6. The IgG2 constant region of claim 5 comprising the sequence of SEQ ID No:9 of FIG. 4.

7. An antibody that specifically binds to human CD3 comprising the mutated IgG2 constant region of claim 1.

8. An antibody that specifically binds to human CD3 comprising the mutated IgG2 constant region of claim 2.

9. The antibody of claim 8, wherein the antibody is humanized.

10. The antibody of claim 9, wherein the antibody is humanized M291.

11. The antibody of claim 10, wherein
the humanized light chain comprises the mature amino acid sequence of SEQ ID No:6 of FIG. 1C and
the humanized heavy chain variable domain comprises the mature amino acid sequence of SEQ ID No:8 of FIG. 1D fused to the IgG2 constant region.

12. The antibody of claim 11, wherein residues 234, 235 and 237 of the mutated IgG2 constant region form the segment ala ala ala.

13. The humanized antibody of claim 10, comprising a humanized heavy chain and a humanized light chain:

(1) the humanized light chain comprising three complementarity determining regions (CDR1, CDR2 and CDR3) having amino acid sequences from the corresponding complementarity determining regions of the mouse M291 immunoglobulin light chain, and a variable region framework from a human kappa light chain variable region framework sequence, and (2) the humanized heavy chain comprising three complementarity determining regions (CDR1, CDR2 and CDR3) having amino acid sequences from the corresponding complementarity determining regions of the mouse M291 immunoglobulin heavy chain, and a variable region framework from a human heavy chain variable region framework sequence except in one to six positions selected from the group consisting of H30, H67, H68, H70, H72 and H74 wherein the amino acid position is occupied by the same amino acid present in the equivalent position of the mouse M291 immunoglobulin heavy chain variable region framework;

wherein the immunoglobulin specifically binds to a CD3 antigen on the surface of T cells with a binding affinity having a lower limit of about $10^7$ $M^{-1}$ and an upper limit of about five-times the binding affinity of the M291 immunoglobulin.

14. The humanized antibody of claim 13, wherein the humanized light chain variable region framework is from the light chain variable region framework of the HF2-1/17 antibody in subgroup I;

the humanized heavy chain region framework is from the heavy chain region variable framework of the 21/28 antibody except in at least one position selected from said group, and except at position 44, wherein the amino acid position is occupied by the same amino acid present in the equivalent position of a human immunoglobulin subgroup I consensus sequence.

15. An antibody comprising the mutated IgG2 constant region of claim 1.

16. An antibody comprising the mutated IgG2 constant region of claim 2.

17. The antibody of claim 15, which is humanized.

18. The antibody of claim 16, which is humanized.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 384 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..384
        ( D ) OTHER INFORMATION: /note= "cDNA for mouse M291 antibody
            light chain variable region"

( x i ) SEQUENCE DESCRIPTION: SEQ ID NO:1:

```
ATG  GAT  TTT  CAA  GTG  CAG  ATT  TTC  AGC  TTC  CTG  CTA  ATC  AGT  GCC  TCA         4 8
Met  Asp  Phe  Gln  Val  Gln  Ile  Phe  Ser  Phe  Leu  Leu  Ile  Ser  Ala  Ser
 1              5                       1 0                     1 5

GCC  ATA  ATA  TCC  AGA  GGA  CAA  ATT  GTT  CTC  ACC  CAG  TCT  CCA  GCA  ATC         9 6
Ala  Ile  Ile  Ser  Arg  Gly  Gln  Ile  Val  Leu  Thr  Gln  Ser  Pro  Ala  Ile
              2 0                      2 5                      3 0

ATG  TCT  GCA  TCT  CCA  GGG  GAG  AAG  GTC  ACC  ATG  ACC  TGC  AGT  GCC  AGC         1 4 4
Met  Ser  Ala  Ser  Pro  Gly  Glu  Lys  Val  Thr  Met  Thr  Cys  Ser  Ala  Ser
              3 5                      4 0                      4 5
```

| | | | | | | | | | | | | | | | | |
|---|---|---|---|---|---|---|---|---|---|---|---|---|---|---|---|---|
| TCA | AGT | GTA | AGT | TAC | ATG | AAC | TGG | TAC | AAG | CAG | AAG | TCA | GGC | ACC | TCC | 192 |
| Ser | Ser | Val | Ser | Tyr | Met | Asn | Trp | Tyr | Lys | Gln | Lys | Ser | Gly | Thr | Ser | |
| | 50 | | | | 55 | | | | | 60 | | | | | | |
| CCC | AAA | AGA | TGG | ACT | TAT | GAC | ACA | TCC | AAA | CTG | GCT | TCT | GGA | GTC | CCT | 240 |
| Pro | Lys | Arg | Trp | Thr | Tyr | Asp | Thr | Ser | Lys | Leu | Ala | Ser | Gly | Val | Pro | |
| 65 | | | | 70 | | | | | 75 | | | | | | 80 | |
| GCT | CGC | TTC | AGT | GGC | AGT | GGG | TCT | GGG | ACC | TCT | TAC | TCT | CTC | ACA | ATC | 288 |
| Ala | Arg | Phe | Ser | Gly | Ser | Gly | Ser | Gly | Thr | Ser | Tyr | Ser | Leu | Thr | Ile | |
| | | | | 85 | | | | | 90 | | | | | 95 | | |
| AGC | AGC | ATG | GAG | GCT | GAA | GAT | GCT | GCC | ACT | TAT | TAC | TGC | CAG | CAG | TGG | 336 |
| Ser | Ser | Met | Glu | Ala | Glu | Asp | Ala | Ala | Thr | Tyr | Tyr | Cys | Gln | Gln | Trp | |
| | | | 100 | | | | | 105 | | | | | 110 | | | |
| AGT | AGT | AAC | CCA | CCC | ACG | TTC | GGC | TCG | GGG | ACA | AAG | TTG | GAA | ATA | AAA | 384 |
| Ser | Ser | Asn | Pro | Pro | Thr | Phe | Gly | Ser | Gly | Thr | Lys | Leu | Glu | Ile | Lys | |
| | | 115 | | | | | 120 | | | | | 125 | | | | |

( 2 ) INFORMATION FOR SEQ ID NO:2:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Asp | Phe | Gln | Val | Gln | Ile | Phe | Ser | Phe | Leu | Leu | Ile | Ser | Ala | Ser |
| 1 | | | | 5 | | | | | 10 | | | | | 15 | |
| Ala | Ile | Ile | Ser | Arg | Gly | Gln | Ile | Val | Leu | Thr | Gln | Ser | Pro | Ala | Ile |
| | | | 20 | | | | | 25 | | | | | 30 | | |
| Met | Ser | Ala | Ser | Pro | Gly | Glu | Lys | Val | Thr | Met | Thr | Cys | Ser | Ala | Ser |
| | | | 35 | | | | | 40 | | | | | 45 | | |
| Ser | Ser | Val | Ser | Tyr | Met | Asn | Trp | Tyr | Lys | Gln | Lys | Ser | Gly | Thr | Ser |
| | 50 | | | | 55 | | | | | 60 | | | | | |
| Pro | Lys | Arg | Trp | Thr | Tyr | Asp | Thr | Ser | Lys | Leu | Ala | Ser | Gly | Val | Pro |
| 65 | | | | 70 | | | | | 75 | | | | | | 80 |
| Ala | Arg | Phe | Ser | Gly | Ser | Gly | Ser | Gly | Thr | Ser | Tyr | Ser | Leu | Thr | Ile |
| | | | | 85 | | | | | 90 | | | | | 95 | |
| Ser | Ser | Met | Glu | Ala | Glu | Asp | Ala | Ala | Thr | Tyr | Tyr | Cys | Gln | Gln | Trp |
| | | | 100 | | | | | 105 | | | | | 110 | | |
| Ser | Ser | Asn | Pro | Pro | Thr | Phe | Gly | Ser | Gly | Thr | Lys | Leu | Glu | Ile | Lys |
| | | 115 | | | | | 120 | | | | | 125 | | | |

( 2 ) INFORMATION FOR SEQ ID NO:3:

( i ) SEQUENCE CHARACTERISTICS:
        ( A ) LENGTH: 417 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..417
        ( D ) OTHER INFORMATION: /note= "cDNA for mouse M291 antibody heavy chain variable region"

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | GAA | AGG | CAC | TGG | ATC | TTT | CTA | CTC | CTG | TTG | TCA | GTA | ACT | GCA | GGT | 48 |
| Met | Glu | Arg | His | Trp | Ile | Phe | Leu | Leu | Leu | Leu | Ser | Val | Thr | Ala | Gly | |
| 1 | | | | 5 | | | | | 10 | | | | | 15 | | |

```
GTC  CAC  TCC  CAG  GTC  CAG  CTG  CAG  CAG  TCT  GGG  GCT  GAA  CTG  GCA  AGA      96
Val  His  Ser  Gln  Val  Gln  Leu  Gln  Gln  Ser  Gly  Ala  Glu  Leu  Ala  Arg
               20                       25                      30

CCT  GGG  GCC  TCA  GTG  AAG  ATG  TCC  TGC  AAG  GCT  TCT  GGC  TAC  ACC  TTT     144
Pro  Gly  Ala  Ser  Val  Lys  Met  Ser  Cys  Lys  Ala  Ser  Gly  Tyr  Thr  Phe
               35                       40                      45

ATT  AGT  TAC  ACG  ATG  CAC  TGG  GTA  AAA  CAG  AGG  CCT  GGA  CAG  GGT  CTG     192
Ile  Ser  Tyr  Thr  Met  His  Trp  Val  Lys  Gln  Arg  Pro  Gly  Gln  Gly  Leu
          50                            55                 60

GAA  TGG  ATT  GGA  TAC  ATT  AAT  CCT  AGA  AGT  GGT  TAT  ACT  CAT  TAC  AAT     240
Glu  Trp  Ile  Gly  Tyr  Ile  Asn  Pro  Arg  Ser  Gly  Tyr  Thr  His  Tyr  Asn
65                       70                       75                          80

CAG  AAG  TTA  AAG  GAC  AAG  GCC  ACA  TTG  ACT  GCA  GAC  AAA  TCC  TCC  AGC     288
Gln  Lys  Leu  Lys  Asp  Lys  Ala  Thr  Leu  Thr  Ala  Asp  Lys  Ser  Ser  Ser
                    85                       90                      95

TCA  GCC  TAC  ATG  CAA  CTG  AGC  AGC  CTG  ACA  TCT  GAG  GAC  TCT  GCA  GTC     336
Ser  Ala  Tyr  Met  Gln  Leu  Ser  Ser  Leu  Thr  Ser  Glu  Asp  Ser  Ala  Val
               100                      105                     110

TAT  TAC  TGT  GCA  AGA  TCG  GCC  TAC  TAT  GAT  TAT  GAC  GGC  TTT  GCT  TAC     384
Tyr  Tyr  Cys  Ala  Arg  Ser  Ala  Tyr  Tyr  Asp  Tyr  Asp  Gly  Phe  Ala  Tyr
          115                      120                     125

TGG  GGC  CAA  GGG  ACT  CTG  GTC  ACT  GTC  TCT  GCA                              417
Trp  Gly  Gln  Gly  Thr  Leu  Val  Thr  Val  Ser  Ala
130                      135
```

( 2 ) INFORMATION FOR SEQ ID NO:4:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Glu  Arg  His  Trp  Ile  Phe  Leu  Leu  Leu  Leu  Ser  Val  Thr  Ala  Gly
1                   5                    10                      15

Val  His  Ser  Gln  Val  Gln  Leu  Gln  Gln  Ser  Gly  Ala  Glu  Leu  Ala  Arg
               20                       25                      30

Pro  Gly  Ala  Ser  Val  Lys  Met  Ser  Cys  Lys  Ala  Ser  Gly  Tyr  Thr  Phe
               35                       40                      45

Ile  Ser  Tyr  Thr  Met  His  Trp  Val  Lys  Gln  Arg  Pro  Gly  Gln  Gly  Leu
          50                            55                 60

Glu  Trp  Ile  Gly  Tyr  Ile  Asn  Pro  Arg  Ser  Gly  Tyr  Thr  His  Tyr  Asn
65                       70                       75                          80

Gln  Lys  Leu  Lys  Asp  Lys  Ala  Thr  Leu  Thr  Ala  Asp  Lys  Ser  Ser  Ser
                    85                       90                      95

Ser  Ala  Tyr  Met  Gln  Leu  Ser  Ser  Leu  Thr  Ser  Glu  Asp  Ser  Ala  Val
               100                      105                     110

Tyr  Tyr  Cys  Ala  Arg  Ser  Ala  Tyr  Tyr  Asp  Tyr  Asp  Gly  Phe  Ala  Tyr
          115                      120                     125

Trp  Gly  Gln  Gly  Thr  Leu  Val  Thr  Val  Ser  Ala
130                      135
```

( 2 ) INFORMATION FOR SEQ ID NO:5:

( i ) SEQUENCE CHARACTERISTICS:
        ( A ) LENGTH: 378 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 1..378
    ( D ) OTHER INFORMATION: /note= "cDNA for humanized mouse M291
        antibody light chain variable region"

( x i ) SEQUENCE DESCRIPTION: SEQ ID NO:5:

| ATG | GAG | ACC | GAT | ACC | CTC | CTG | CTA | TGG | GTC | CTC | CTG | CTA | TGG | GTC | CCA | 48 |
|---|---|---|---|---|---|---|---|---|---|---|---|---|---|---|---|---|
| Met | Glu | Thr | Asp | Thr | Leu | Leu | Leu | Trp | Val | Leu | Leu | Leu | Trp | Val | Pro | |
| 1 | | | | 5 | | | | | 10 | | | | | 15 | | |
| GGA | TCA | ACC | GGA | GAT | ATT | CAG | ATG | ACC | CAG | TCT | CCA | TCT | TCC | CTC | TCT | 96 |
| Gly | Ser | Thr | Gly | Asp | Ile | Gln | Met | Thr | Gln | Ser | Pro | Ser | Ser | Leu | Ser | |
| | | | 20 | | | | | 25 | | | | | 30 | | | |
| GCT | AGC | GTC | GGG | GAT | AGG | GTC | ACC | ATA | ACC | TGC | TCT | GCC | AGC | TCA | AGT | 144 |
| Ala | Ser | Val | Gly | Asp | Arg | Val | Thr | Ile | Thr | Cys | Ser | Ala | Ser | Ser | Ser | |
| | | 35 | | | | | 40 | | | | | 45 | | | | |
| GTA | AGT | TAC | ATG | AAC | TGG | TAC | CAG | CAG | AAG | CCA | GGC | AAA | GCT | CCC | AAG | 192 |
| Val | Ser | Tyr | Met | Asn | Trp | Tyr | Gln | Gln | Lys | Pro | Gly | Lys | Ala | Pro | Lys | |
| | 50 | | | | | 55 | | | | | 60 | | | | | |
| AGA | CTA | ATT | TAT | GAC | ACA | TCC | AAA | CTG | GCT | TCT | GGA | GTC | CCT | TCT | AGG | 240 |
| Arg | Leu | Ile | Tyr | Asp | Thr | Ser | Lys | Leu | Ala | Ser | Gly | Val | Pro | Ser | Arg | |
| 65 | | | | | 70 | | | | | 75 | | | | | 80 | |
| TTC | AGT | GGC | AGT | GGA | TCT | GGG | ACC | GAT | TTC | ACC | CTC | ACA | ATC | AGC | TCT | 288 |
| Phe | Ser | Gly | Ser | Gly | Ser | Gly | Thr | Asp | Phe | Thr | Leu | Thr | Ile | Ser | Ser | |
| | | | | 85 | | | | | 90 | | | | | 95 | | |
| CTG | CAG | CCA | GAA | GAT | TTC | GCC | ACT | TAT | TAC | TGC | CAG | CAA | TGG | AGT | AGT | 336 |
| Leu | Gln | Pro | Glu | Asp | Phe | Ala | Thr | Tyr | Tyr | Cys | Gln | Gln | Trp | Ser | Ser | |
| | | | 100 | | | | | 105 | | | | | 110 | | | |
| AAC | CCA | CCC | ACG | TTC | GGT | GGA | GGG | ACC | AAG | GTG | GAG | ATC | AAA | | | 378 |
| Asn | Pro | Pro | Thr | Phe | Gly | Gly | Gly | Thr | Lys | Val | Glu | Ile | Lys | | | |
| | | 115 | | | | | 120 | | | | | 125 | | | | |

( 2 ) INFORMATION FOR SEQ ID NO:6:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Glu | Thr | Asp | Thr | Leu | Leu | Leu | Trp | Val | Leu | Leu | Leu | Trp | Val | Pro |
|---|---|---|---|---|---|---|---|---|---|---|---|---|---|---|---|
| 1 | | | | 5 | | | | | 10 | | | | | 15 | |
| Gly | Ser | Thr | Gly | Asp | Ile | Gln | Met | Thr | Gln | Ser | Pro | Ser | Ser | Leu | Ser |
| | | | 20 | | | | | 25 | | | | | 30 | | |
| Ala | Ser | Val | Gly | Asp | Arg | Val | Thr | Ile | Thr | Cys | Ser | Ala | Ser | Ser | Ser |
| | | 35 | | | | | 40 | | | | | 45 | | | |
| Val | Ser | Tyr | Met | Asn | Trp | Tyr | Gln | Gln | Lys | Pro | Gly | Lys | Ala | Pro | Lys |
| | 50 | | | | | 55 | | | | | 60 | | | | |
| Arg | Leu | Ile | Tyr | Asp | Thr | Ser | Lys | Leu | Ala | Ser | Gly | Val | Pro | Ser | Arg |
| 65 | | | | | 70 | | | | | 75 | | | | | 80 |
| Phe | Ser | Gly | Ser | Gly | Ser | Gly | Thr | Asp | Phe | Thr | Leu | Thr | Ile | Ser | Ser |
| | | | | 85 | | | | | 90 | | | | | 95 | |
| Leu | Gln | Pro | Glu | Asp | Phe | Ala | Thr | Tyr | Tyr | Cys | Gln | Gln | Trp | Ser | Ser |
| | | | 100 | | | | | 105 | | | | | 110 | | |
| Asn | Pro | Pro | Thr | Phe | Gly | Gly | Gly | Thr | Lys | Val | Glu | Ile | Lys | | |
| | | 115 | | | | | 120 | | | | | 125 | | | |

( 2 ) INFORMATION FOR SEQ ID NO:7:

( i ) SEQUENCE CHARACTERISTICS:
  ( A ) LENGTH: 417 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 1..417
  ( D ) OTHER INFORMATION: /note= "cDNA for humanized mouse M291 antibody heavy chain variable region"

( x i ) SEQUENCE DESCRIPTION: SEQ ID NO:7:

| ATG | GGA | TGG | AGC | TGG | ATC | TTT | CTC | TTC | CTC | CTG | TCA | GGT | ACC | GCG | GGC | 48 |
|---|---|---|---|---|---|---|---|---|---|---|---|---|---|---|---|---|
| Met | Gly | Trp | Ser | Trp | Ile | Phe | Leu | Phe | Leu | Leu | Ser | Gly | Thr | Ala | Gly | |
| 1 | | | | 5 | | | | | 10 | | | | | 15 | | |

| GTG | CAC | TCT | CAG | GTC | CAG | CTT | GTC | CAG | TCT | GGG | GCT | GAA | GTC | AAG | AAA | 96 |
|---|---|---|---|---|---|---|---|---|---|---|---|---|---|---|---|---|
| Val | His | Ser | Gln | Val | Gln | Leu | Val | Gln | Ser | Gly | Ala | Glu | Val | Lys | Lys | |
| | | | 20 | | | | | 25 | | | | | 30 | | | |

| CCT | GGC | GCC | AGC | GTG | AAG | GTC | TCC | TGC | AAG | GCT | TCT | GGC | TAC | ACC | TTT | 144 |
|---|---|---|---|---|---|---|---|---|---|---|---|---|---|---|---|---|
| Pro | Gly | Ala | Ser | Val | Lys | Val | Ser | Cys | Lys | Ala | Ser | Gly | Tyr | Thr | Phe | |
| | | 35 | | | | | 40 | | | | | 45 | | | | |

| ATT | AGC | TAC | ACG | ATG | CAT | TGG | GTA | AGG | CAG | GCC | CCT | GGA | CAG | GGT | CTG | 192 |
|---|---|---|---|---|---|---|---|---|---|---|---|---|---|---|---|---|
| Ile | Ser | Tyr | Thr | Met | His | Trp | Val | Arg | Gln | Ala | Pro | Gly | Gln | Gly | Leu | |
| | 50 | | | | | 55 | | | | | 60 | | | | | |

| GAA | TGG | ATG | GGA | TAT | ATT | AAT | CCG | AGA | AGT | GGG | TAT | ACT | CAT | TAC | AAT | 240 |
|---|---|---|---|---|---|---|---|---|---|---|---|---|---|---|---|---|
| Glu | Trp | Met | Gly | Tyr | Ile | Asn | Pro | Arg | Ser | Gly | Tyr | Thr | His | Tyr | Asn | |
| 65 | | | | | 70 | | | | | 75 | | | | | 80 | |

| CAG | AAG | TTA | AAG | GAC | AAG | GCA | ACA | CTT | ACC | GCG | GAC | AAA | TCC | GCG | AGC | 288 |
|---|---|---|---|---|---|---|---|---|---|---|---|---|---|---|---|---|
| Gln | Lys | Leu | Lys | Asp | Lys | Ala | Thr | Leu | Thr | Ala | Asp | Lys | Ser | Ala | Ser | |
| | | | | 85 | | | | | 90 | | | | | 95 | | |

| ACA | GCC | TAC | ATG | GAA | CTG | AGC | AGC | CTG | AGA | TCT | GAG | GAC | ACC | GCA | GTC | 336 |
|---|---|---|---|---|---|---|---|---|---|---|---|---|---|---|---|---|
| Thr | Ala | Tyr | Met | Glu | Leu | Ser | Ser | Leu | Arg | Ser | Glu | Asp | Thr | Ala | Val | |
| | | | 100 | | | | | 105 | | | | | 110 | | | |

| TAT | TAC | TGT | GCA | AGA | TCG | GCC | TAC | TAT | GAT | TAT | GAC | GGC | TTT | GCT | TAC | 384 |
|---|---|---|---|---|---|---|---|---|---|---|---|---|---|---|---|---|
| Tyr | Tyr | Cys | Ala | Arg | Ser | Ala | Tyr | Tyr | Asp | Tyr | Asp | Gly | Phe | Ala | Tyr | |
| | | 115 | | | | | 120 | | | | | 125 | | | | |

| TGG | GGC | CAA | GGA | ACC | CTG | GTC | ACA | GTC | TCC | TCA | | | | | | 417 |
|---|---|---|---|---|---|---|---|---|---|---|---|---|---|---|---|---|
| Trp | Gly | Gln | Gly | Thr | Leu | Val | Thr | Val | Ser | Ser | | | | | | |
| 130 | | | | | 135 | | | | | | | | | | | |

( 2 ) INFORMATION FOR SEQ ID NO:8:

( i ) SEQUENCE CHARACTERISTICS:
  ( A ) LENGTH: 139 amino acids
  ( B ) TYPE: amino acid
  ( D ) TOPOLOGY: linear ( i i ) MOLECULE TYPE: protein ( x i ) SEQUENCE DESCRIPTION: SEQ ID NO:8:

| Met | Gly | Trp | Ser | Trp | Ile | Phe | Leu | Phe | Leu | Leu | Ser | Gly | Thr | Ala | Gly |
|---|---|---|---|---|---|---|---|---|---|---|---|---|---|---|---|
| 1 | | | | 5 | | | | | 10 | | | | | 15 | |

| Val | His | Ser | Gln | Val | Gln | Leu | Val | Gln | Ser | Gly | Ala | Glu | Val | Lys | Lys |
|---|---|---|---|---|---|---|---|---|---|---|---|---|---|---|---|
| | | | 20 | | | | | 25 | | | | | 30 | | |

| Pro | Gly | Ala | Ser | Val | Lys | Val | Ser | Cys | Lys | Ala | Ser | Gly | Tyr | Thr | Phe |
|---|---|---|---|---|---|---|---|---|---|---|---|---|---|---|---|
| | | 35 | | | | | 40 | | | | | 45 | | | |

| Ile | Ser | Tyr | Thr | Met | His | Trp | Val | Arg | Gln | Ala | Pro | Gly | Gln | Gly | Leu |
|---|---|---|---|---|---|---|---|---|---|---|---|---|---|---|---|
| | 50 | | | | | 55 | | | | | 60 | | | | |

| Glu | Trp | Met | Gly | Tyr | Ile | Asn | Pro | Arg | Ser | Gly | Tyr | Thr | His | Tyr | Asn |
|---|---|---|---|---|---|---|---|---|---|---|---|---|---|---|---|
| 65 | | | | | 70 | | | | | 75 | | | | | 80 |

```
Gln Lys Leu Lys Asp Lys Ala Thr Leu Thr Ala Asp Lys Ser Ala Ser
                85                  90                  95

Thr Ala Tyr Met Glu Leu Ser Ser Leu Arg Ser Glu Asp Thr Ala Val
                100                 105                 110

Tyr Tyr Cys Ala Arg Ser Ala Tyr Tyr Asp Tyr Asp Gly Phe Ala Tyr
            115                 120                 125

Trp Gly Gln Gly Thr Leu Val Thr Val Ser Ser
            130                 135
```

( 2 ) INFORMATION FOR SEQ ID NO:9:

( i ) SEQUENCE CHARACTERISTICS:
        ( A ) LENGTH: 326 amino acids
        ( B ) TYPE: amino acid
        ( C ) STRANDEDNESS:
        ( D ) TOPOLOGY: linear ( i i ) MOLECULE TYPE: protein ( i x ) FEATURE:
        ( A ) NAME/KEY: Protein
        ( B ) LOCATION: 1..326
        ( D ) OTHER INFORMATION: /note= "heavy chain constant region of
            IgG2 mutant 3"

( x i ) SEQUENCE DESCRIPTION: SEQ ID NO:9:

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Ala Ala Ala Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

|  |  |  |  |  |  |  |  |  |  |  |  |  |  |  |
|---|---|---|---|---|---|---|---|---|---|---|---|---|---|---|
| Ala | Val | Glu | Trp 260 | Glu | Ser | Asn | Gly | Gln 265 | Pro | Glu | Asn | Asn | Tyr 270 | Lys | Thr |
| Thr | Pro | Pro 275 | Met | Leu | Asp | Ser | Asp 280 | Gly | Ser | Phe | Phe | Leu 285 | Tyr | Ser | Lys |
| Leu | Thr 290 | Val | Asp | Lys | Ser | Arg 295 | Trp | Gln | Gln | Gly | Asn 300 | Val | Phe | Ser | Cys |
| Ser 305 | Val | Met | His | Glu | Ala 310 | Leu | His | Asn | His | Tyr 315 | Thr | Gln | Lys | Ser | Leu 320 |
| Ser | Leu | Ser | Pro | Ser 325 | Lys |

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GGACACCTTC TCTCCTCCC                                     19

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CCCAAGCTTG GGTGGGCCGA GCCGGCCTCT GTCC               34

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GCACCACCTG CGGCAGGACC GTCA                           24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

TGACGGTCCT GCCGCAGGTG GTGC                           24